United States Patent
Strang et al.

(10) Patent No.: US 11,020,343 B2
(45) Date of Patent: Jun. 1, 2021

(54) INTRANASAL PHARMACEUTICAL DOSAGE FORMS COMPRISING NALOXONE

(71) Applicant: HARM REDUCTION THERAPEUTICS, INC., Bethesda, MD (US)

(72) Inventors: John Strang, Denmark Hill (GB); Alexander Oksche, Limburg (DE); Stephen Harris, Stamford, CT (US); Kevin Smith, Cambridge (GB); Lucie Helene Jeanne Mottier, Cambridge (GB)

(73) Assignee: Harm Reduction Therapeutics, Inc., Bethesda, MD (US)

( * ) Notice: Subject to any disclaimer, the term of this patent is extended or adjusted under 35 U.S.C. 154(b) by 0 days.

(21) Appl. No.: 16/549,838

(22) Filed: Aug. 23, 2019

(65) Prior Publication Data

US 2019/0374464 A1     Dec. 12, 2019

Related U.S. Application Data

(63) Continuation of application No. 15/418,138, filed on Jan. 27, 2017, now abandoned, which is a continuation of application No. 14/084,551, filed as application No. PCT/EP2012/058792 on May 11, 2012, now abandoned.

(30) Foreign Application Priority Data

May 13, 2011 (EP) ..................... 11166076

(51) Int. Cl.
*A61K 31/485* (2006.01)
*A61K 9/00* (2006.01)
*A61K 47/02* (2006.01)

(52) U.S. Cl.
CPC .......... *A61K 9/0043* (2013.01); *A61K 9/0019* (2013.01); *A61K 31/485* (2013.01); *A61K 47/02* (2013.01)

(58) Field of Classification Search
CPC ................................................... A61K 31/485
See application file for complete search history.

(56) References Cited

U.S. PATENT DOCUMENTS

| | | | |
|---|---|---|---|
| 4,464,378 A | 8/1984 | Hussain | |
| 5,629,011 A | 5/1997 | Illum | |
| 5,866,154 A * | 2/1999 | Bahal | A61K 9/0019 424/423 |
| 6,284,765 B1 | 9/2001 | Caffrey | |
| 6,387,917 B1 | 5/2002 | Illum et al. | |
| 6,608,073 B1 | 8/2003 | Hussain et al. | |
| 6,677,346 B1 | 1/2004 | Achari et al. | |
| 7,666,876 B2 | 2/2010 | Birch et al. | |
| 2004/0115133 A1 | 6/2004 | Wermeling et al. | |
| 2006/0009447 A1 | 1/2006 | Merkus | |
| 2006/0110333 A1 | 5/2006 | Yanagawa | |
| 2007/0212307 A1 | 9/2007 | Wermeling et al. | |
| 2008/0153879 A1 | 6/2008 | Watts et al. | |
| 2008/0260848 A1 | 10/2008 | Nagata et al. | |
| 2009/0047234 A1 | 2/2009 | Touitou et al. | |

FOREIGN PATENT DOCUMENTS

| | | |
|---|---|---|
| CN | 1575795 A | 2/2005 |
| EP | 2 116 264 A1 | 11/2009 |
| GB | 2403711 A | 1/2005 |
| JP | 2002-541921 A | 12/2002 |
| JP | 2005-527535 A | 9/2005 |
| RU | 2 344 822 C2 | 1/2009 |
| WO | WO 82/03768 | 11/1982 |
| WO | WO 00/62757 | 10/2000 |
| WO | WO 02/11778 A1 | 2/2002 |
| WO | WO 02/051380 A1 | 7/2002 |
| WO | WO 03/080022 A2 | 10/2003 |
| WO | 2009/040595 * | 4/2009 |
| WO | WO 2009/040595 A1 | 4/2009 |

OTHER PUBLICATIONS

Wang et al. CN 1575795A, 2004 (i.e., a English-translated version).*
NARCAN®, 1971.*
Darke, S., et al., "The Ratio of Non-Fatal Heroin Overdose," *Addiction* 98:1169-1172, Society for the Study of Addiction to Alcohol and Other Drugs, England (2003).
Dowling, J., et al., "Population Pharmacokinetics of Intravenous, Intramuscular, and Intranasal Naloxone in Human Volunteers," *Ther Drug Monit* 30(4):490-496, Lippincott Williams & Wilkins, United States (2008).
Hall, W.D., et al., "How many dependent heroin users are there in Australia?" *The Medical Journal of Australia* 173(10):528-531, Australian Medical Publishing Co., Australia (2000).
Kerr, D., et al., "Randomized controlled trial comparing the effectiveness and safety of intranasal and intramuscular naloxone for the treatment of suspected heroin overdose," *Addiction* 104:2067-2074, Society for the Study of Addiction, England (2009).
Loimer, N., et al., "Nasal Administration of Naloxone is as Effective as the Intravenous Route in Opiate Addicts," *The International Journal of the Addictions* 29(6):819-827, Marcel Dekker, Inc., United States (1994).

(Continued)

*Primary Examiner* — Rei Tsang Shiao
(74) *Attorney, Agent, or Firm* — Lowenstein Sandler LLP

(57) ABSTRACT

The present invention relates to an intranasal pharmaceutical dosage form comprising a dosing unit comprising naloxone or a pharmaceutically acceptable salt thereof in an amount of equivalent to ≥0.5 mg naloxone HC dissolved in an application fluid of a volume of ≤250 μl. Furthermore, the present invention relates to such an intranasal pharmaceutical dosage form for use in the treatment of opioid overdosing and/or at least one symptom thereof.

13 Claims, 16 Drawing Sheets

(56) References Cited

OTHER PUBLICATIONS

Wilburn, S.Q., "Needlestick and Sharps Injury Prevention," *The Online Journal of Issues in Nursing* 9(3):10 pages, American Nurses Association, United States (2004).

International Search Report for International Application No. PCT/EP2012/058792, European Patent Office, Netherlands, dated Mar. 20, 2013.

Wermeling, D.P., "Opioid Harm Reduction Strategies: Focus on Expanded Access Intranasal Naloxone," *Pharmacotherapy* 30(7):627-631, Pharmacotherapy Publications, United States (2010).

Nadejdin, A.V., et al., "Possibility of use of low doses of naloxone upon the treatment of heroin addiction," *S.S. Korsakov Journal of Neurology and Psychiatry* 106(1):56-57 (2006).

Nadejdin, A.V., et al., "Possibility of use of low doses of naloxone upon the treatment of heroin addiction," *S.S. Korsakov Journal of Neurology and Psychiatry* 106(1):56-57 (2006) (English Translation).

"Management of substance abuse, Information sheet on opioid overdose," who.int, accessed at http://www.who.int/substance_abuse/information-sheet/en/ accessed on Sep. 11, 2017, 4 pages (2014).

Kelly, A.M. and Koutsogiannis, Z., "Intranasal naloxone for life threatening opioid toxicity," *Emerg Med J.* 19(4):375, BMJ Pub. Group, England (2002).

U.S. Department of Health and Human Services Food and Drug Administration Center for Evaluation and Research, "Guidance for Industry Estimating the Maximum Safe Starting Dose in Initial Clinical Trials for Therapeutics in Adult Healthy Volunteers," accessed at http://www.fda.gov/downloads/Drugs/.../Guidances/UCM078932.pdf, 30 pages (Jul. 2005).

Merlin, M.A., et al., "Intranasal naloxone delivery is an alternative to intravenous naloxone for opioid overdoses," *American Journal of Emergency Medicine* 28:296-303, Elsevier, United States (2010).

Office Action dated Sep. 7, 2017, in U.S. Appl. No. 15/590,466, Strang, J., et al., filed May 9, 2017, 6 pages.

Office Action dated Mar. 23, 2018, in U.S. Appl. No. 15/590,466, Strang, J., et al., filed May 9, 2017, 6 pages.

\* cited by examiner

Figure 2

| Mean Pharmacokinetic Parameters for Naloxone | | | | |
|---|---|---|---|---|
| | 8 mg Intranasal Naloxone (N = 11) | 16 mg Intranasal Naloxone (N = 12) | 16 mg Sublingual Naloxone (N = 11) | 1 mg Intravenous Naloxone (N = 11) |
| **AUCt (pg*h/mL)** | | | | |
| n | 11 | 12 | 11 | 11 |
| Mean | 20069.7 | 32814.8 | 2670.9 | 10464.8 |
| SD | 4927.13 | 10217.67 | 1779.24 | 7150.09 |
| Median | 19469.3 | 33244.3 | 2033.3 | 6639.9 |
| Min, Max | 12217, 29753 | 20875, 58270 | 913, 6867 | 5001, 26850 |
| Geometric Mean | 19535.4 | 31520.4 | 2259.3 | 8865.6 |
| **AUCinf (pg*h/mL)** | | | | |
| n | 4 | 4 | 4 | 3 |
| Mean | 22040.5 | 42753.6 | 1504.9 | 12605.6 |
| SD | 4237.15 | 10590.72 | 419.97 | 12415.05 |
| Median | 21838.1 | 38670.2 | 1550.6 | 5868.2 |
| Min, Max | 17068, 27418 | 35272, 58402 | 958, 1960 | 5016, 26933 |
| Geometric Mean | 21734.3 | 41886.1 | 1456.4 | 9255.0 |
| Cmax (pg/mL) | | | | |
| n | 11 | 12 | 11 | 11 |
| Mean | 12833.6 | 18251.0 | 897.1 | 17877.5 |
| SD | 4474.71 | 7501.83 | 365.22 | 29858.65 |
| Median | 12781.0 | 16948.5 | 934.0 | 4668.0 |
| Min, Max | 5791, 19192 | 9776, 30198 | 378, 1587 | 3250, 100297 |
| Geometric Mean | 12070.5 | 16930.4 | 827.9 | 8149.6 |
| tmax (h) | | | | |
| n | 11 | 12 | 11 | 11 |
| Mean | 0.34 | 0.39 | 3.91 | 0.85 |
| SD | 0.171 | 0.230 | 10.645 | 1.563 |
| Median | 0.33 | 0.33 | 0.67 | 0.07 |
| Min, Max | 0.07, 0.50 | 0.07, 0.67 | 0.50, 36.00 | 0.03, 4.00 |
| Lambda z (1/h) | | | | |
| n | 4 | 4 | 4 | 3 |
| Mean | 0.08 | 0.08 | 0.63 | 0.78 |
| SD | 0.033 | 0.023 | 0.138 | 0.067 |
| Median | 0.08 | 0.08 | 0.60 | 0.76 |
| Min, Max | 0.05, 0.13 | 0.06, 0.10 | 0.51, 0.83 | 0.74, 0.86 |
| T1/2 (h) | | | | |
| n | 4 | 4 | 4 | 3 |
| Mean | 9.48 | 9.09 | 1.13 | 0.89 |
| SD | 3.893 | 2.723 | 0.221 | 0.073 |
| Median | 8.86 | 8.62 | 1.16 | 0.91 |
| Min, Max | 5.46, 14.75 | 6.66, 12.47 | 0.84, 1.37 | 0.80, 0.94 |

INTRANASAL PHARMACEUTICAL DOSAGE FORMS COMPRISING NALOXONE

FIELD OF THE INVENTION

The present invention relates to an intranasal pharmaceutical dosage form comprising a dosing unit comprising naloxone or a pharmaceutically acceptable salt thereof in an amount of equivalent to ≥0.5 mg naloxone HCl, preferably an amount of equivalent to between about 0.65 mg naloxone HCl and about 0.8 mg naloxone HCl or between about 1.3 mg naloxone HCl and about 1.6 mg naloxone HCl, dissolved in an application fluid of a volume of ≥250 μC. Preferably, the dosage form is for use in the treatment of opioid overdosing and/or at least one symptom thereof.

BACKGROUND OF THE INVENTION

The abuse of opioids, in particular the intravenous injection of opioids such as heroin by drug addicts is quite often associated with overdosing of the drug which can be due to a loss of opioid tolerance (e.g. when abusers are imprisoned or following substitution/detoxification therapy), wrong estimation of the amount of the drug consumed, a more concentrated form of the drug, or the abuser's desire to produce a "high" despite the drug tolerance developed over time. It has been estimated that the rate for overdosing in addicts is between 19% and 30% (Darke S et al. "The ratio of non-fatal to fatal heroin overdose; Addiction, 2003 August; 98(8): 1169-71). Such overdosing incidents can lead to the death of the addict (so called "fatal overdosing"). The annual mortality rate of addicts due to heroin overdosing has been reported to be 0.8% (Hall et al.; "How many dependent heroin users are there in Australia?" Med J Aust. 2000 Nov. 20; 173(10):528-31 2000). The ratio of non-fatal to fatal overdosing has been estimated to be between 23.8 to 1 and 37.5 to 1 (Darke et al, see above). Thus, non-fatal overdosing represents a considerable number of events among drug addicts, especially in drug addicts who abuse the drug parenterally, i.e. by injection, requiring an adequate instant treatment by emergency health care personnel.

Naloxone, an opioid antagonist, is known to counteract the actions of opioids and is used in opioid overdosing emergency cases and in rapid opiate detoxification.

Since the onset of action of naloxone used in such cases should be as fast as possible, naloxone is thus far mainly administered intravenously or intramuscularly by emergency health care personnel to the subject with an overdosing.

Due to a high first pass metabolism, oral dosage forms comprising naloxone display a low bioavailability and thus seem to be not suitable for such purposes.

The administration of naloxone via injection into the blood stream or into the muscle requires first of all trained medical personnel (for intravenous injection) or a trained career (for intramuscular injection). Secondly, depending on the constitution of the addict and the period of intravenous drug abuse, it can be particularly difficult to find access into a vein of the addict's body for administering naloxone intravenously.

Clearly, there is a risk of exposure to blood borne pathogens for the medical personnel or the trained career since a large population of drug addicts suffers from blood borne pathogen induced diseases such as HIV, hepatitis B and C, and the like since accidental needlestick is a serious safety concern. 385,000 needle-stick injuries have been estimated to occur in the year 2000 in the US only (Wilburn, "Needlestick and sharps injury prevention, Online J Issues Nurs 2004 Sep. 30; 9(3):5).

Furthermore, due to the relatively short elimination half life of naloxone administered intravenously, there is the need to re-administer naloxone, in some cases even several times, via this route.

There have been studies on the intranasal administration of naloxone in order to treat addicts with overdosing. However, their outcome is rather controversial. Thus, Loimer et al. reported that the nasal administration of naloxone is as effective as the intravenous route in opiate addicts (see Loimer N. et al, "Nasal administration of naloxone is as effective as the intravenous route in opiate addicts"; the International Journal of Addictions, 29(6), 819-827, 1994). Dowling et al., on the other hand, reported that naloxone administered intranasally displays a relative bioavailability of 4% only and concluded that the intranasal absorption is rapid but does not maintain measurable concentrations for more than an hour (Dowling et al., "Population pharmacokinetics of intravenous, intramuscular, and intranasal naloxone in human volunteers", Ther Drug Monit, Vol 30, No 4, August 2008).

Thus, there is a general need for a naloxone dosage form which can easily be administered to drug addicts suffering from overdosing by medically untrained subjects, e.g. by family members or other careers.

Furthermore, even if administered by health care personnel, such dosage form should i) minimize the danger of being exposed to blood borne pathogens and ii) reduce administration time as there is no need for identifying injectable veins or undressing the subject for intramuscular injection. Also, such dosage forms should display a fast onset of action and ideally maintain a counteracting effect over a period of several hours.

OBJECTS AND SUMMARY OF THE INVENTION

It is thus one objective of the present invention to provide a pharmaceutical dosage form comprising naloxone which exhibits a considerably high bioavailability of naloxone combined with a fast onset of action and a relatively long period of action.

It is another objective of the present invention to provide such a dosage form for use in the treatment of opioid overdosing and/or at least one symptom thereof.

Still another object of the present invention resides in the use of naloxone or a pharmaceutically acceptable salt thereof in a specific amount dissolved in a specific volume for a dosing unit of such a dosage form.

These and other objects as they will become apparent from the ensuing description are attained by the subject matter of the independent claims. The dependent claims relate to some of the preferred embodiments of the present invention.

Thus, the present invention is in one aspect concerned with an intranasal pharmaceutical dosage form comprising a dosing unit comprising naloxone or a pharmaceutically acceptable salt thereof in an amount of equivalent to ≥0.5 mg naloxone HCl dissolved in an application fluid of a volume of ≤250 μl.

In a preferred embodiment, the amount of naloxone or a pharmaceutically acceptable salt thereof is equivalent to ≥0.6 mg.

In another preferred embodiment, the amount of naloxone or a pharmaceutically acceptable salt thereof is equivalent to between about 0.65 mg naloxone HCl and about 0.8 mg naloxone HCl or between about 1.3 mg naloxone HCl and about 1.6 mg naloxone HCl.

In a particularly preferred embodiment, the present invention relates to an intranasal pharmaceutical dosage form comprising naloxone or a pharmaceutically acceptable salt thereof dissolved in an application fluid, wherein an amount of equivalent to between about 1.3 mg naloxone HCl and about 1.6 mg naloxone HCl is administered intranasally, wherein said amount is provided by administration to one nostril or wherein said amount is provided by administration to two nostrils, and wherein the volume of the application fluid per nostril is ≥250 µl.

In a further preferred embodiment, the volume of the application fluid is ≤200 µl.

In a particularly preferred embodiment, the amount of naloxone or a pharmaceutically acceptable salt thereof is within a range of equivalent to 0.6 mg naloxone HCl to 12 mg naloxone HCl, preferably equivalent to 0.6 mg naloxone HCl to 6 mg naloxone HCl, more preferably equivalent to 0.6 mg naloxone HCl to 3.75 mg naloxone HCl, and most preferably equivalent to 0.6 mg naloxone HCl to 2.0 mg naloxone HCl. Said range can also be within a range of equivalent to 0.5 mg naloxone HCl to 20 mg naloxone HCl, or within a range of equivalent to 0.5 mg naloxone HCl to 15 mg naloxone HCl, or within a range of equivalent to 0.5 mg naloxone HCl to 10 mg naloxone HCl. Most preferred is a range of equivalent to between about 0.65 mg naloxone HCl and about 0.8 mg naloxone HCl or between about 1.3 mg naloxone HCl and about 1.6 mg naloxone HCl.

In another preferred embodiment, an amount of naloxone or a pharmaceutically acceptable salt thereof equivalent to about 1.3 mg naloxone HCl or about 1.4 mg naloxone HCl or about 1.5 mg naloxone HCl or about 1.6 mg naloxone HCl is administered intranasally, wherein said amount is provided by administration to one nostril or wherein said amount is provided by administration to two nostrils, and wherein the volume of the application fluid per nostril is ≥250 µl.

In still another preferred embodiment, the volume of the application fluid is within a range of 200 µl to 35 µl, preferably of 200 µl to 50 µl, more preferably of 200 µl to 100 µl, and most preferably of 150 µl to 100 µl. Said range may also be a range of 250 µl to 35 µl, or 250 µl to 75 µl, or 200 µl to 75 µl. Particularly preferred is a volume of 200 µl, or 150 µl, or 100 µl, or 50 µl. For some cases, a volume of 75 µl may also be used.

In yet another preferred embodiment, the amount of naloxone or a pharmaceutically acceptable salt thereof is equivalent to 0.6 mg naloxone HCl, or 0.7 mg naloxone HCl, or 0.8 mg naloxone HCl, or 1.2 mg naloxone HCl, or 1.4 mg naloxone HCl, or 1.6 mg naloxone HCl, and the volume of the application fluid is within a range of 200 µl to 50 µl, preferably of 200 µl to 100 µl, and more preferably of 150 µl to 100 µl. It can also be preferred that the amount of naloxone or a pharmaceutically acceptable salt thereof is equivalent to 0.9 mg naloxone HCl, or 1.0 mg naloxone HCl, or 1.1 mg naloxone HCl, or 1.8 mg naloxone HCl, or 2.0 mg naloxone HCl, or 2.2 mg naloxone HCl wherein the volume ranges above are applicable.

In still another preferred embodiment, the final concentration of the naloxone or a pharmaceutically acceptable salt thereof in the application fluid is within a range of equivalent to 3 mg naloxone HCl per ml application fluid to 100 mg naloxone HCl per ml application fluid, preferably within a range of equivalent to 3 mg naloxone HCl per ml application fluid to 70 mg naloxone HCl per ml application fluid, and more preferably within a range of equivalent to 3 mg naloxone HCl per ml application fluid to 24 mg naloxone HCl per ml application fluid.

Preferably, the dosing unit of the intranasal dosage form as claimed herein is administered to a single nostril. Thus, preferably, the above mentioned amount of naloxone or a pharmaceutically acceptable salt thereof is provided by administration to one nostril.

Due to the presence of two nostrils, one application step as defined below may be comprised of the consecutive administration of two dosing units, each to one of the two nostrils. The following preferred embodiments relate to such an application step, i.e. the consecutive administration to the two nostrils. Most preferably, such an application step via the consecutive administration to two nostrils results in the intranasal administration of a naloxone amount of equivalent to between about 1.3 mg naloxone HCl and about 1.6 mg naloxone HCl.

In a particularly preferred embodiment, the amount of naloxone or a pharmaceutically acceptable salt thereof is within a range of equivalent to 0.6 mg naloxone HCl to 6 mg naloxone HCl, preferably equivalent to 0.6 mg naloxone HCl to 3 mg naloxone HCl, more preferably equivalent to 0.6 mg naloxone HCl to 1.8 mg naloxone HCl, and most preferably equivalent to 0.6 mg naloxone HCl to 1.0 mg naloxone HCl. Said range can also be within a range of equivalent to 0.5 mg naloxone HCl to 10 mg naloxone HCl, or within a range of equivalent to 0.5 mg naloxone HCl to 7.5 mg naloxone HCl, or within a range of equivalent to 0.5 mg naloxone HCl to 5 mg naloxone HCl.

In still another preferred embodiment, the volume of the application fluid is within a range of 200 µl to 35 µl, preferably of 200 µl to 50 µl, more preferably of 200 µl to 100 µl, and most preferably of 150 µl to 100 µl. Said range may also be a range of 250 µl to 35 µl, or 250 µl to 75 µl, or 200 µl to 75 µl. Particularly preferred is a volume of 200 µl, or 150 µl, or 100 µl. For some cases, a volume of 75 µl may also be used.

In yet another preferred embodiment, the amount of naloxone or a pharmaceutically acceptable salt thereof is equivalent to 0.6 mg naloxone HCl or 0.7 mg naloxone HCl or 0.8 mg naloxone HCl, and the volume of the application fluid is within a range of 200 µl to 50 µl, preferably of 200 µl to 100 µl, and more preferably of 150 µl to 100 µl. It can also be preferred that the amount of naloxone or a pharmaceutically acceptable salt thereof is equivalent to 0.9 mg naloxone HCl, or 1.0 mg naloxone HCl, or 1.1 mg naloxone HCl, wherein the volume ranges above are applicable.

In still another preferred embodiment, the final concentration of the naloxone or a pharmaceutically acceptable salt thereof in the application fluid is within a range of equivalent to 3 mg naloxone HCl per ml application fluid to 100 mg naloxone HCl per ml application fluid, preferably within a range of equivalent to 3 mg naloxone HCl per ml application fluid to 70 mg naloxone HCl per ml application fluid, and more preferably within a range of equivalent to 3 mg naloxone HCl per ml application fluid to 12 mg naloxone HCl per ml application fluid.

Due to the presence of two nostrils, one application step as defined below may also be comprised of a single administration to one of the two nostrils only. The following preferred embodiments relate to such an application step, i.e. the single administration to one nostril only. Most preferably, such an application step to one nostril only results in the intranasal administration of a naloxone amount of equivalent to between about 1.3 mg naloxone HCl and about 1.6 mg naloxone HCl.

In a particularly preferred embodiment, the amount of naloxone or a pharmaceutically acceptable salt thereof is within a range of equivalent to 1.2 mg naloxone HCl to 12 mg naloxone HCl, preferably equivalent to 1.2 mg naloxone HCl to 6 mg naloxone HCl, more preferably equivalent to 1.2 mg naloxone HCl to 3.75 mg naloxone HCl, and most preferably equivalent to 1.2 mg naloxone HCl to 2.0 mg naloxone HCl. Said range can also be within a range of equivalent to 1.0 mg naloxone HCl to 20 mg naloxone HCl, or within a range of equivalent to 1.0 mg naloxone HCl to 15 mg naloxone HCl, or within a range of equivalent to 1.0 mg naloxone HCl to 10 mg naloxone HCl.

In still another preferred embodiment, the volume of the application fluid is within a range of 200 µl to 35 µl, preferably of 200 µl to 50 µl, more preferably of 200 µl to 100 µl, and most preferably of 150 µl to 100 µl. Said range may also be a range of 250 µl to 35 µl, or 250 µl to 75 µl, or 200 µl to 75 µl. Particularly preferred is a volume of 200 µl, or 150 µl, or 100 µl. For some cases, a volume of 75 µl may also be used.

In yet another preferred embodiment, the amount of naloxone or a pharmaceutically acceptable salt thereof is equivalent to 1.2 mg naloxone HCl or 1.4 mg naloxone HCl or 1.6 mg naloxone HCl, and the volume of the application fluid is within a range of 200 µl to 50 µl, preferably of 200 µl to 100 µl, and more preferably of 150 µl to 100 µl. It can also be preferred that the amount of naloxone or a pharmaceutically acceptable salt thereof is equivalent to 1.8 mg naloxone HCl, or 2.0 mg naloxone HCl, or 2.2 mg naloxone HCl, wherein the volume ranges above are applicable.

In still another preferred embodiment, the final concentration of the naloxone or a pharmaceutically acceptable salt thereof in the application fluid is within a range of equivalent to 6 mg naloxone HCl per ml application fluid to 100 mg naloxone HCl per ml application fluid, preferably within a range of equivalent to 6 mg naloxone HCl per ml application fluid to 70 mg naloxone HCl per ml application fluid, and more preferably within a range of equivalent to 6 mg naloxone HCl per ml application fluid to 24 mg naloxone HCl per ml application fluid.

In yet another preferred embodiment relating to all embodiments above, the application fluid is selected from the group comprising water, an aqueous solution optionally comprising a pharmaceutical solvent, an aqueous solution comprising a pharmaceutical solvent and co-solvent and an aqueous saline solution. Preferably, the aqueous saline solution is a NaCl solution, more preferably NaCl in purified water at a concentration of about 1.0% weight/volume, most preferably NaCl in purified water at concentration of about 0.9% weight/volume. Preferably, the pH-value of the application fluid corresponds to a pH≤about 6.0, preferably to a pH≤about 5.8, more preferably to a pH≤about 5.6 and most preferably to a pH≤about 5.5.

In another preferred embodiment, the dosage form comprises at least two dosage units, preferably at least three dosage units, more preferably at least four dosage units and most preferably at least five dosage units. The dosage form may also comprise only one dosage unit, or exactly two, three, four, or five dosage units.

Generally, the dosage form may comprise the above mentioned amount or half of said amount dissolved in an application fluid in a dosing unit, the amount being dependent on whether said total amount is provided by administration to one nostril or by administration to two nostrils. Thus, if said amount is administered to one nostril, the dosage form preferably comprises said total amount dissolved in an application fluid in a dosing unit. If said amount is administered to two nostrils, the dosage form preferably comprises half of said total amount dissolved in an application fluid in a dosing unit.

Preferably, said dosing unit comprises naloxone or a pharmaceutically acceptable salt thereof in an amount of equivalent to between about 0.65 mg naloxone HCl and about 0.8 mg naloxone HCl if a single application step comprises the administration to two nostrils. About 0.65 mg, about 0.70 mg, about 0.75 mg or about 0.80 mg may be particularly preferred.

Preferably, said dosing unit comprises naloxone or a pharmaceutically acceptable salt thereof in an amount of equivalent to between about 1.3 mg naloxone HCl and about 1.6 mg naloxone HCl if a single application step comprises the administration to one nostril. About 1.30 mg, about 1.35 mg, about 1.40 mg, about 1.45 mg, about 1.50 mg, about 1.55 mg or about 1.60 mg may be particularly preferred.

A dosage form may comprise a single dosing unit only and may thus be for single use if said amount is administered to one nostril. If said amount is administered to two nostrils, the dosage form may comprise two dosing units and may still be for single use. However, said dosage form may also comprise at least two dosing units, preferably at least three dosing units, more preferably at least four dosing units and most preferably at least five dosing units and may thus be for multiple uses.

In still another preferred embodiment, the dosage form is selected from the group of dosage forms comprising a nasal spray (which may also be referred to as spraying device), a nasal mucoadhesive dosage form and a Mucosal Atomizer Device. A nasal spray may be particularly preferred for the present invention. Said nasal spray may particularly be a syringe-driven spraying device or a pump-driven spraying device.

Preferably, the dosage form comprises naloxone as the only pharmaceutically active agent. Thus, no further pharmaceutically active agent(s) such as e.g. epinephrine may be comprised in the dosage form.

In yet another preferred embodiment, the dosage form provides for a high bioavailability of the active agent naloxone in humans, preferably for a bioavailability of about 20% to about 40%, more preferably of about 25% to about 35%, as determined against a reference of intravenously administration naloxone with a bioavailability set to 100%.

In still another preferred embodiment, the dosage form provides for a fast onset of action of the active agent naloxone in humans, i.e. a low tmax, preferably a fast onset of action within about 5 minutes to about 18 minutes upon administration, preferably within about 5 minutes to about 12 minutes upon administration, more preferably within about 5 minutes to about 10 minutes upon administration and most preferably within about 6 minutes upon administration.

In yet another preferred embodiment, the dosage form provides for a long plasma half-live of the active agent naloxone in humans, i.e. a slow elimination pattern, preferably a plasma half-live of about 1.5 hours to about 9 hours upon administration, more preferably a plasma half-live of about 2.5 hours to about 9 hours upon administration and most preferably a plasma half-live of about 4 hours to about 9 hours upon administration. The plasma half-live of the active agent naloxone in humans can also be about 1 hour, about 1.5 hours, about 2 hours, about 3 hours, about 4 hours, about 5 hours, about 6 hours, about 7 hours, about 8 hours or about 9 hours upon administration of the dosage form according to the present invention.

In a second aspect, the present invention is concerned with the treatment of opioid overdosing and/or at least one symptom thereof.

Thus, in said aspect, the above mentioned dosage form including all preferred embodiments mentioned above is for use in the treatment of opioid overdosing and/or at least one symptom thereof.

In a particularly preferred embodiment, the present invention relates to an intranasal pharmaceutical dosage form comprising naloxone or a pharmaceutically acceptable salt thereof dissolved in an application fluid for use in the treatment of opioid overdosing and/or at least one symptom thereof, wherein an amount of equivalent to between about 1.3 mg naloxone HCl and about 1.6 mg naloxone HCl is administered intranasally, wherein said amount is provided by administration to one nostril or wherein said amount is provided by administration to two nostrils, and wherein the volume of the application fluid per nostril is ≤ about 250 µl, preferably ≤ about 200 µl.

The present invention therefore also relates to a method of treating opioid overdosing and/or at least one symptom thereof, wherein naloxone or a pharmaceutically acceptable salt thereof is administered intranasally in an amount of equivalent to ≥0.5 mg naloxone HCl in an application of a volume of ≤ 250 µl.

The opioid overdosing may be due to the misuse of heroin, buprenorphine, methadone, fentanyl, oxycodone, morphine and hydromorphone. Thus, the opioid overdosing may be caused by the illicit use of opioids. However, the opioid overdosing may also be caused by an accidental misuse of opioids during opioid therapy.

In a preferred embodiment, the opioid overdosing symptom is selected from the group comprising respiratory depression, optionally postoperative opioid respiratory depression, altered level consciousness, miotic pupils, hypoxemia, acute lung injury and aspiration pneumonia.

In a further preferred embodiment, the dosage form is re-applied during an initial titration period in order to provide for an effective amount of naloxone. The above mentioned amount may thus be re-administered during an initial titration period in order to provide for an effective amount of naloxone when used for treating an opioid overdosing and/or at least one symptom thereof. Preferably, said initial titration period is a period of about 15 to about 30 minutes starting with the first application step. It can be preferred to re-apply the dosage form according to the present invention two times, three times, four times, five times or even six times in order to provide for an amount of naloxone effective in treating opioid overdosing and/or at least one symptom thereof.

In another preferred embodiment, the dosage form according to the present invention is combined with an intramuscular and/or intravenous dosage form comprising naloxone or a pharmaceutically acceptable salt thereof. It can be preferred that said intramuscular and/or intravenous dosage form comprises naloxone or a pharmaceutically acceptable salt thereof in amounts ranging from about 0.4 mg to about 2 mg.

The present invention is also concerned in one aspect with the use of naloxone or a pharmaceutically acceptable salt thereof in an amount of equivalent to ≥1.0 mg naloxone HCl, preferably of between about 0.65 mg naloxone HCl and about 0.8 mg naloxone HCl or between about 1.3 mg naloxone HCl and about 1.6 mg naloxone HCl, dissolved in an application fluid of a volume of ≤250 µl in a dosing unit of an intranasal pharmaceutical dosage form.

In preferred embodiments, all the amounts of naloxone and volumes of the application fluid as mentioned above can be used in a dosing unit of an intranasal pharmaceutical dosage form.

BRIEF DESCRIPTION OF THE FIGURES

FIG. 2 shows the pharmacokinetic parameters of the study described in Example 1.

DETAILED DESCRIPTION OF THE INVENTION

Figure 1:
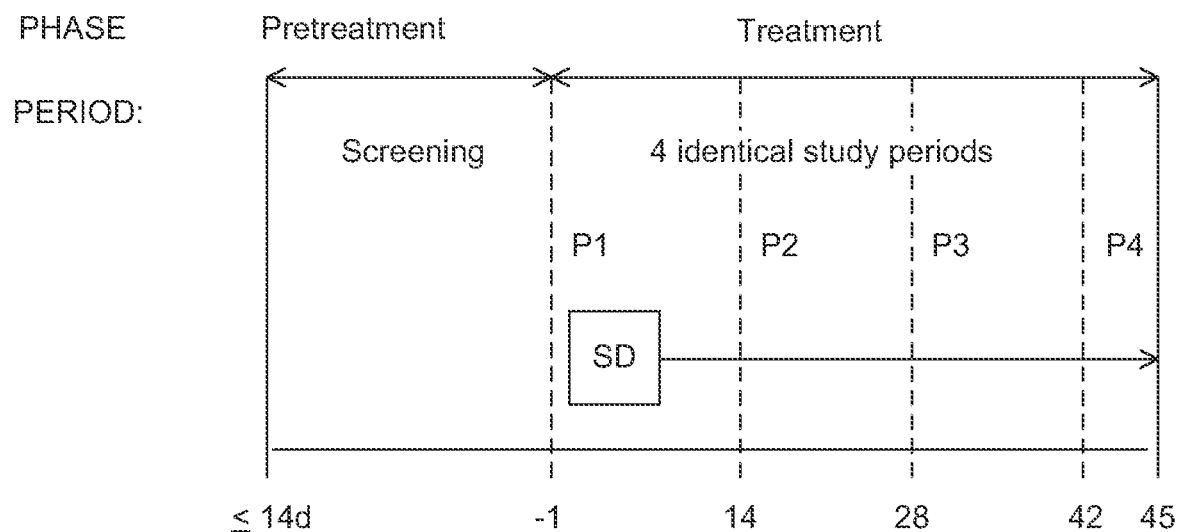
FIG. 1 depicts the phases of the study described in Example 1, with:
SD: study drug according to random sequence code
P1-P4: Periods 1-4 each identical with a single dose of study drug according to random sequence code, followed by a ≥14 day washout (Periods 1, 2 and 3 only).

The present invention partially resides in the surprising finding that an intranasal pharmaceutical dosage form comprising naloxone or a pharmaceutically acceptable salt thereof dissolved in an application fluid of a volume of ≤250 Cl displays a significant bioavailability, fast onset of action and a relatively slow elimination pattern.

For use in opioid overdosing, such an intranasal dosage form may thus include in a dosing unit an amount of naloxone effective to counteract the actions of the opioid, wherein the dosage form is an easy-to-use and safe dosage form with the pharmacokinetic parameters set out above, namely a significant bioavailability, fast onset of action and a relatively slow elimination pattern.

Before some of the embodiments of the present invention are described in more detail, the following definitions are introduced.

As used in the specification and the claims, the singular forms of "a" and "an" also include the corresponding plurals unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of 10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

"Naloxone" as referred to herein is a commercially available narcotic antagonist, which is indicated for the blockade of exogenously administered opioids. It acts at all opioid receptor sites ($\mu$, $\kappa$, and $\delta$). Following oral administration, naloxone is rapidly absorbed (within 5-30 minutes) but has a very low oral bioavailability of <3% due to an extensive first-pass-metabolism. In low oral doses, naloxone does not become systemically available but acts mainly on local opioid receptors in the gastrointestinal tract. In cases of opioid overdoses, naloxone reverses the effects of the abused opioids and is thus used in order to treat overdosing.

The term "a pharmaceutically acceptable salt" of naloxone refers e.g. to the hydrochloride salt, the sulfate salt, the bisulfate salt, the tartrate salt, the nitrate salt, the citrate salt, the bitartrate salt, the phosphate salt, the malate salt, the maleate salt, the hydrobromide salt, the hydroiodide salt, the fumerate salt, the succinate salt and the like. Naloxone may also be present as base addition salts such as the metal salt of alkali metals including lithium, sodium and potassium. A preferred salt is the hydrochloride salt of naloxone.

The term "intranasal dosage form" as used herein is defined as a pharmaceutical dosage form which releases the active agent within the nose. Upon release, the active agent is transported subsequently into the systemic circulation via the nasal mucosa. Typically, a specific dosing unit or metered volume is applied from the intranasal dosage form to one nostril of the nose per administration step. In order to provide for the complete dosing unit or complete metered volume, it may be necessary to carry out at least one priming step of the intranasal dosage form prior to the administration. In case of a nasal spray, this mean for example that the nasal spray is pumped outside the nose for at least one time until the pump of the spray is completely filled with the metered volume to be applied.

The term "dosing unit" as used herein refers to a specific amount of the active agent which is administered in a single administration step to a single nostril. As set out below, such an amount may be e.g. 0.6 mg naloxone HCl per nostril in the initial step of treating an opioid overdosing. Preferably, said amount may be equivalent to between about 1.3 mg naloxone HCl and about 1.6 mg naloxone HCl in a dosing unit if the total amount is provided by administration to one nostril only in a single application step. Alternatively, said amount may be equivalent to between about 0.65 mg naloxone HCl and about 0.8 mg naloxone HCl in a dosing unit if the total amount is provided by administration to two nostrils in a single application step. Since the naloxone or pharmaceutically acceptable salt thereof is dissolved in an application fluid to a specific final concentration, the amount administered per single administration step corresponds to a specific volume to be administered. In the present invention, said volume is preferably ≤200 µl.

The intranasal dosage form of the present invention may e.g. be a nasal spray. It is clear to the skilled person that a nasal spray will in most cases not only comprise a final volume of ≤200 µl. Rather, said nasal spray may e.g. comprise 1.5 ml, wherein a volume of e.g. 100 µl is administered per administration step, i.e. as metered volume per application. As set out above, priming of the spray may be necessary prior to the application.

The skilled person is aware that due to the presence of two nostrils, intranasal dosage forms may be administered in a dosage regimen divided into two consecutive steps, namely a first administration step of half of the amount of the active agent to be administered into one nostril, followed by the administration of the other half into the other nostril. This "divided" way of administration is preferred for the present invention since smaller volumes per nostril may be used.

In a particularly preferred embodiment, the present invention thus relates to an intranasal pharmaceutical dosage form comprising naloxone or a pharmaceutically acceptable salt thereof, wherein an amount of equivalent to between about 1.3 mg naloxone HCl and about 1.6 mg naloxone HCl is administered intranasally, wherein said amount is provided by administration to two nostrils, and wherein the volume of the application fluid per nostril is ≥250 µl. An amount of equivalent to between about 0.65 mg naloxone HCl and about 0.8 mg naloxone HCl may thus be administered per nostril, arriving at the above total amount.

However, one may also administer the active agent in a single administration step into one nostril. Using an identical volume per nostril as for the divided administration to two nostrils, it is obvious for the skilled person that the concentration of the active agent in the administration fluid then needs to be twice the concentration in order to provide for the same amount of the active agent.

In another particularly preferred embodiment, the present invention thus relates to an intranasal pharmaceutical dosage form comprising naloxone or a pharmaceutically acceptable salt thereof, wherein an amount of equivalent to between 1.3 mg naloxone HCl and about 1.6 mg naloxone HCl is administered intranasally, wherein said amount is provided by administration to one nostril, and wherein the volume of the application fluid per nostril is ≤250 µl. The amount of equivalent to between 1.3 mg naloxone HCl and about 1.6 mg naloxone HCl may thus be administered to one nostril only.

Generally, a pharmaceutical dosage form comprises an active agent in a specific amount in order to achieve a specific effect. Thus, an active agent may e.g. be comprised in an amount of 10 mg in a tablet, i.e. an oral dosage form. By administering such a tablet in one application step to a patient, the effective amount of 10 mg is provided in the patient's body. As already discussed above, the situation differs for an intranasal administration of an active agent due to the presence of two nostrils. In this respect, it needs to be understood that the final amount of an active agent administered intranasally is always the therapeutically active amount, regardless of whether the administration regimen comprises a single administration step to one nostril only or two consecutive administration steps to two nostrils. Both ways, either the single administration step or the two consecutive administration steps are referred to herein as "one application step" in the meaning of providing the desired therapeutically active amount, e.g. 1.2 mg or an amount of equivalent to between 1.3 mg naloxone HCl and about 1.6 mg naloxone HCl.

The term "application fluid" as used herein preferably refers to a solution comprising the active agent in a dissolved state. However, "application fluid" as used herein may also refer to a suspension comprising at least some of the active agent (and optionally further ingredients) in a solid phase dispersed throughout a fluid phase. When reference to a suspension is made, the term "dissolved" is thus used in the meaning of "dispersed". As mentioned below, the formulation used may also be a gel or a gel-like formulation. Accordingly, the term "application fluid" also refers to gel or gel-like phases.

The term "bioavailability" as used herein refers to the extent of an active agent in the systemic circulation and the rate at which an active agent enters the systemic circulation. The bioavailability of an active agent with respect to different dosage forms can inter alia be evaluated by comparing the AUCt-value (see below) provided by a dosage form to be analyzed (e.g. an intranasal dosage form) with the AUCt-value provided by an intravenous dosage form. Thus, the bioavailability expressed in % may be calculated by dividing the AUCt-value of the dosage form to be analyzed and the AUCt-value of the intravenous dosage form, and multiplying by factor 100.

The "Cmax value" indicates the maximum blood plasma concentration of the active agent naloxone.

The "tmax value" indicates the time point at which the Cmax value is reached. In other words, tmax is the time point of the maximum observed plasma concentration.

The "AUC (Area Under the Curve)" value corresponds to the area under the plasma concentration-time curve. The AUC value is proportional to the amount of the active agent naloxone absorbed into the blood circulation in total and is hence a measure for the bioavailability.

The "AUCt value" is the value for the area under the plasma concentration-time curve from the time of administration to the last measurable concentration. AUCt values are usually calculated using the linear trapezoidal method.

"LambdaZ", which is the terminal phase rate constant, is estimated using those points determined to be in the terminal log-linear phase.

"t½", also termed "t½z", which is the apparent terminal phase half-life, is commonly determined from the ratio of ln 2 to LambdaZ.

The areas under the plasma concentration-time curve between the last measured point and infinity may be calculated from the ratio of the final observed plasma concentration (Clast) to LambdaZ. This is then added to the AUCt to yield "AUCinf", which is the area under the plasma concentration-time curve from the time of administration to infinity.

The inventors have surprisingly found that an intranasal pharmaceutical dosage form as described herein exhibits upon administration an early appearance in the systemic circulation indicated by a low tmax combined with relatively long plasma half-life of the naloxone in the systemic circulation. Moreover, the dosage forms according to the present invention also display a reasonably high bioavailability in the range of between about 25% and about 35%.

Without being bound to a scientific theory, the inventors assume at present that said remarkable effects of an early tmax and/or a relatively long elimination half-life (i.e. a sustained action of naloxone) and/or a rather high bioavailability could be due to rapid absorption of the whole amount of naloxone at the nasal mucous membrane which displays a high vascularization. In order to achieve this effect, it appears to be essential to administer the naloxone in a small volume such that the loss due to swallowing (which would correspond to oral administration with a low bioavailability, see above), leaking from the nostrils, and the like is avoided. Therefore, preferably small volumes below 0.5 ml of application fluid, more preferably below 0.25 ml application fluid should be used for the administration. Generally, the volumes may be in the range of 30 µl to 400 µl, 35 µl to 350 µl, 40 µl to 300 µl, 50 µl to 250 µl, 60 µl to 200 µl, 70 µl to 150 µl, or 80 µl to 120 µl.

The present invention is to be seen in the background of immediate medical care in emergency situations, namely in case of opioid overdosing. In most cases, the overdosing is due to an intravenous abuse of opioids and may result in unconsciousness of the abuser. With the present invention at hand, naloxone may be administered in order to counter the overdosing of the opioid in a safe and efficient way, namely by intranasal administration.

Moreover, naloxone may be administered by a family member, a friend or a career of the opioid addict immediately when being confronted with the overdose situation. Thus, treatment can be initiated even prior to the arrival of emergency health care personnel which clearly reduces the risk of either a fatal outcome of the overdosing or major sequelae due to the overdosing. In such a scenario, family members, friends or other careers should thus be provided with an intranasal dosage form according to the present invention when living with a subject having potential for an overdosing of opioids.

Since naloxone needs to be present in the systemic circulation of the abuser in a concentration sufficient to counter the effect of the opioid, an effective amount of naloxone has to be provided in one application step. However, depending on the abuser and the severity of the overdosing, this effective amount varies and it may thus be necessary to carry out a titration by repeated application steps within a relatively short time until the effective amount is reached.

Typically, the effective amount of naloxone can be determined by assessing the subject's respiratory rate, wherein an increase in the respiratory rate indicates the countering effect of naloxone. If such an increase should not be detectable upon about 5 to about 10 minutes after administration of the first naloxone dose, a second dose should be administered, followed again by an assessment of the subject's respiratory rate. If two or several application steps are necessary in order to reach the effective dose of naloxone, this is typically referred to as "titration". In the present case, such titration steps are usually carried out within the first 15 to 20 minutes.

A particularly preferred typical starting amount for an intravenous administration of naloxone corresponds to about 0.4 mg IV when treating an opioid overdose and/or a symptom thereof (see also Example 2 of the present application). With the present surprising finding (e.g. with respect to the intranasal bioavailability of naloxone), a most preferred starting amount of naloxone administered intranasally for use in the treatment of opioid overdosing and/or at least one symptom thereof thus corresponds to an amount equivalent to between about 1.3 mg naloxone HCl and about 1.6 mg naloxone HCl (wherein said amount is provided by administration to one nostril or wherein said amount is provided by administration to two nostrils). Amounts of naloxone equivalent to about 1.3 mg naloxone HCl, about 1.4 mg naloxone HCl, about 1.5 mg naloxone HCl, and about 1.6 mg naloxone HCl may be particularly preferred as typical starting amounts.

Another typical starting point for an effective amount of naloxone may be an amount of equivalent to about 1.2 mg naloxone HCl administered intranasally in one application step.

Thus, one may administer a volume of 200 µl application fluid comprising naloxone in a concentration of equivalent to 6 mg naloxone HCl per ml administration fluid into a single nostril in order to provide for an amount of 1.2 mg naloxone HCl. Alternatively, a volume of 100 µl application fluid comprising naloxone in a concentration of equivalent to 6 mg naloxone HCl per ml administration fluid can be administered into the first nostril, followed by the administration of another 100 µl application fluid comprising naloxone in a concentration of equivalent to 6 mg naloxone HCl per ml administration fluid into the second nostril.

Alternatively, one may administer a volume of 150 µl application fluid comprising naloxone in a concentration of equivalent to 8 mg naloxone HCl per ml administration fluid into a single nostril in order to provide for an amount of 1.2 mg naloxone HCl. Alternatively, a volume of 75 µl application fluid comprising naloxone in a concentration of equivalent to 8 mg naloxone HCl per ml administration fluid may be administered into the first nostril, followed by the administration of another 75 µl application fluid comprising naloxone in a concentration of equivalent to 8 mg naloxone HCl per ml administration fluid into the second nostril.

Still alternatively, one may administer a volume of 100 µl application fluid comprising naloxone in a concentration of equivalent to 12 mg naloxone HCl per ml administration fluid into a single nostril in order to provide for an amount of 1.2 mg naloxone HCl. Alternatively, a volume of 50 µl application fluid comprising naloxone in a concentration of equivalent to 12 mg naloxone HCl per ml administration fluid may be administered into the first nostril, followed by the administration of another 50 µl application fluid comprising naloxone in a concentration of equivalent to 12 mg naloxone HCl per ml administration fluid into the second nostril.

Another typical starting point for an effective amount may be an amount of equivalent to about 1.6 mg naloxone HCl administered intranasally in one application step.

Thus, one may administer a volume of 200 µl application fluid comprising naloxone in a concentration of equivalent to 8 mg naloxone HCl per ml administration fluid into a single nostril in order to provide for an amount of 1.6 mg naloxone HCl. Alternatively, a volume of 100 µl application fluid comprising naloxone in a concentration of equivalent to 8 mg naloxone HCl per ml administration fluid can be administered into the first nostril, followed by the administration of another 100 µl application fluid comprising naloxone in a concentration of equivalent to 8 mg naloxone HCl per ml administration fluid into the second nostril.

Alternatively, one may administer a volume of 150 µl application fluid comprising naloxone in a concentration of equivalent to 10.7 mg naloxone HCl per ml administration fluid into a single nostril in order to provide for an amount of 1.6 mg naloxone HCl. Alternatively, a volume of 75 µl application fluid comprising naloxone in a concentration of equivalent to 10.7 mg naloxone HCl per ml administration fluid may be administered into the first nostril, followed by the administration of another 75 µl application fluid comprising naloxone in a concentration of equivalent to 10.7 mg naloxone HCl per ml administration fluid into the second nostril.

Still alternatively, one may administer a volume of 100 µl application fluid comprising naloxone in a concentration of equivalent to 16 mg naloxone HCl per ml administration fluid into a single nostril in order to provide for an amount of 1.6 mg naloxone HCl. Alternatively, a volume of 50 µl application fluid comprising naloxone in a concentration of equivalent to 16 mg naloxone HCl per ml administration fluid may be administered into the first nostril, followed by the administration of another 50 µl application fluid comprising naloxone in a concentration of equivalent to 16 mg naloxone HCl per ml administration fluid into the second nostril.

Still another typical starting point for an effective amount may be an amount of equivalent to about 2.4 mg naloxone HCl administered intranasally in one application step.

Thus, one may administer a volume of 200 µl application fluid comprising naloxone in a concentration of equivalent to 12 mg naloxone HCl per ml administration fluid into a single nostril in order to provide for an amount of 2.4 mg naloxone HCl. Alternatively, a volume of 100 µl application fluid comprising naloxone in a concentration of equivalent to 12 mg naloxone HCl per ml administration fluid can be administered into the first nostril, followed by the administration of another 100 µl application fluid comprising naloxone in a concentration of equivalent to 12 mg naloxone HCl per ml administration fluid into the second nostril.

Alternatively, one may administer a volume of 150 µl application fluid comprising naloxone in a concentration of equivalent to 16 mg naloxone HCl per ml administration fluid into a single nostril in order to provide for an amount of 2.4 mg naloxone HCl. Alternatively, a volume of 75 µl application fluid comprising naloxone in a concentration of equivalent to 16 mg naloxone HCl per ml administration fluid may be administered into the first nostril, followed by the administration of another 75 µl application fluid comprising naloxone in a concentration of equivalent to 16 mg naloxone HCl per ml administration fluid into the second nostril.

Still alternatively, one may administer a volume of 100 µl application fluid comprising naloxone in a concentration of equivalent to 24 mg naloxone HCl per ml administration fluid into a single nostril in order to provide for an amount of 2.4 mg naloxone HCl. Alternatively, a volume of 50 µl application fluid comprising naloxone in a concentration of equivalent to 24 mg naloxone HCl per ml administration fluid may be administered into the first nostril, followed by the administration of another 50 µl application fluid comprising naloxone in a concentration of equivalent to 24 mg naloxone HCl per ml administration fluid into the second nostril.

Yet another typical starting point for an effective amount may be an amount of equivalent to about 3.2 mg naloxone HCl administered intranasally in one application step.

Thus, one may administer a volume of 200 µl application fluid comprising naloxone in a concentration of equivalent to 16 mg naloxone HCl per ml administration fluid into a single nostril in order to provide for an amount of 3.2 mg naloxone HCl. Alternatively, a volume of 100 µl application fluid comprising naloxone in a concentration of equivalent to 16 mg naloxone HCl per ml administration fluid can be administered into the first nostril, followed by the administration of another 100 µl application fluid comprising naloxone in a concentration of equivalent to 16 mg naloxone HCl per ml administration fluid into the second nostril.

Alternatively, one may administer a volume of 150 µl application fluid comprising naloxone in a concentration of equivalent to 21.4 mg naloxone HCl per ml administration fluid into a single nostril in order to provide for an amount of 3.2 mg naloxone HCl. Alternatively, a volume of 75 µl application fluid comprising naloxone in a concentration of equivalent to 21.4 mg naloxone HCl per ml administration fluid may be administered into the first nostril, followed by the administration of another 75 µl application fluid comprising naloxone in a concentration of equivalent to 21.4 mg naloxone HCl per ml administration fluid into the second nostril.

Still alternatively, one may administer a volume of 100 µl application fluid comprising naloxone in a concentration of equivalent to 32 mg naloxone HCl per ml administration fluid into a single nostril in order to provide for an amount of 3.2 mg naloxone HCl. Alternatively, a volume of 50 µl application fluid comprising naloxone in a concentration of equivalent to 32 mg naloxone HCl per ml administration fluid may be administered into the first nostril, followed by the administration of another 50 µl application fluid comprising naloxone in a concentration of equivalent to 32 mg naloxone HCl per ml administration fluid into the second nostril.

It can also be preferred to start with an amount of equivalent to 4 mg naloxone HCl, 6 mg naloxone HCl, 8 mg naloxone HCl, 10 mg naloxone HCl, 12 mg naloxone HCl, 14 mg naloxone HCl or 16 mg naloxone HCl, wherein said amounts are preferably provided in 2×100 µl application fluid for two consecutive administrations to two nostrils in one application step. It might be preferred to exclude an amount of equivalent to 1 mg or 2 mg naloxone HCl administered intranasally as starting point.

It needs to be understood that the above mentioned second administration step, i.e. the consecutive administration to the second nostril, is not regarded in the present invention as a repeated administration for titration purposes. Rather, as outlined above, the administration to the first nostril and the administration to the second nostril are regarded as one application step.

It can generally be preferred to administer the naloxone in one application step comprised of two consecutive administration steps, each comprising 100 µl application fluid, to the two nostrils. It can further be preferred for such an application step that the concentration of naloxone or a pharmaceutically acceptable salt thereof in the application fluid is between equivalent to 6 mg naloxone HCl per ml application fluid and 80 mg naloxone HCl per ml application fluid, preferably between equivalent to 10 mg naloxone HCl per ml application fluid and 70 mg naloxone HCl per ml application fluid, more preferably between equivalent to 20 mg naloxone HCl per ml application fluid and 60 mg naloxone HCl per ml application fluid, and most preferably between equivalent to 20 mg naloxone HCl per ml application fluid and 50 mg naloxone HCl per ml application fluid. In this setup, a particularly preferred concentration of naloxone or a pharmaceutically acceptable salt thereof in the application fluid is between equivalent to 18 mg naloxone HCl per ml application fluid and 20 mg naloxone HCl per ml application fluid Should the starting dose be insufficient as effective naloxone dose, another application step may be necessary. In this case, a titration to the effective amount is carried out (see above). Thus, a second dose may be administered, wherein said second dose preferably corresponds to the initial first dose administered, i.e. it can be equivalent to 1.2 mg naloxone HCl, 1.6 mg naloxone HCl, 2.4 mg naloxone HCl or 3.2 mg naloxone HCl. In a preferred embodiment, said second dose may correspond to an amount equivalent to between about 1.3 mg naloxone HCl and about 1.6 mg naloxone HCl (wherein said amount is provided by administration to one nostril or wherein said amount is provided by administration to two nostrils).

As for the first dose, the administration of the second dose may comprise a single administration step only, i.e. to one nostril, or may comprise two consecutive administration steps to two nostrils in order to provide for the one application step.

In some cases, it may be necessary to apply a third dose or even a fourth or fifth dose of naloxone in separate application steps in order to achieve the desired effect.

It needs to be understood that all the above mentioned application steps are to be seen as steps carried out during the initial treatment phase, typically within the first about 15 to about 30 minutes. As already mentioned above, the inventors have surprisingly found that a slow elimination pattern is achieved by the present invention. Thus, a repeated administration of naloxone may not be necessary.

In some overdosing cases, it may, however, be necessary to re-administer naloxone intranasally or by a different route in order to maintain the countering effect. Such a re-administration may e.g. be necessary after about 2, 3, 4, 5 or 6 hours following the first administration (wherein the first administration may include several application steps during the initial titration).

When re-administering naloxone via the intranasal route, the same doses and volumes as indicated above may be used. Thus, said re-administration dose preferably corresponds to the first dose administered.

In another preferred embodiment, at least one of the intranasal pharmaceutical dosage form as described herein is combined with an intramuscular and/or intravenous dosage form comprising naloxone. Thus, the intranasal pharmaceutical dosage form may be administered prior to or subsequent to the administration of the intramuscular and/or intravenous dosage form comprising naloxone. Such a combined administration may be necessary depending on the condition of the subject to be treated and will usually be judged by trained medical personnel. When combining the present intranasal administration with an intramuscular and/or intravenous administration, it can be preferred that about 0.4 mg to about 2 mg naloxone are administered intramuscularly and/or intravenously.

As can be deduced from the example section of the present invention, an intranasal dosage form comprising naloxone dissolved in a small volume provides for a low tmax, a high bioavailability and a relatively long elimination half-life.

Compared to oral dosage forms comprising naloxone, the bioavailability exhibited by the intranasal dosage form of the present invention seems to be higher by a factor of at least about 10. Also, the tmax seems to be lower compared to the tmax of an oral dosage form.

Compared to intravenously administered naloxone, wherein the bioavailability is set to 100% (and used as reference), the bioavailability of a dosage form of the present invention seems to be reasonably high. Intravenously administered naloxone displays a fast onset of action within about 1 to 2 minutes, which seems to be only slightly faster than the onset of action by a dosage form of the present invention.

As confirmed by the study described in the example section of the present invention, intravenously administered naloxone exhibits an elimination half life of about 60 to 90 minutes. This rather short elimination half life of intravenously administered naloxone requires a repeated administration or a continuous infusion in order to avoid the recurrence of the symptoms of opioid overdosing, such as e.g. respiratory depression.

Clearly, this intravenous re-administration or continuous infusion is accompanied with drawbacks such as the need for qualified medical personnel with the repeated danger of needlestick injury or the need to monitor a continuous infusion by such personnel. This may be overcome by the dosage form of the present invention since the intranasal dosage forms of the present invention display an elimination half life of about several hours.

Thus the pharmaceutical dosage forms of the present invention seem to be particularly suitable in order to be administered in case of an opioid overdosing in order to reverse the overdosing and/or the symptoms thereof, such as e.g. respiratory depression.

Preferably, the intranasal dosage form is a nasal spray, a nasal mucoadhesive dosage form or a Mucosal Atomizer Device, all of which can easily be administered not only by trained medical personnel but also by a medically untrained subject. For the present indication, it is preferred that the intranasal dosage form corresponds to a device capable of functioning in a supine position as well as in upright position; such devices are clearly preferred in the present invention (see also device referred to above).

The formulation which is used in the intranasal dosage form may be a solution, a suspension or a nasal gel/gel-like formulation. Gel or gel-like formulations may particularly be used if additional sustained release of naloxone is aimed at.

Typical pharmaceutical excipients used in intranasal formulations are known to the skilled person and can be used for the formulations according to the present invention. This includes absorption/permeability enhancer as well as binders, carriers and the like which are known to the skilled person. The skilled person is further aware that other typical reagents such as a tonicity agent, a buffer, a solvent, a co-solvent, a viscosity agent or a gelling agent may be use in the formulation.

Particularly preferred is the use of a nasal spray. Thus, one may e.g. use a nasal spray comprising a dosing unit comprising naloxone or a pharmaceutically acceptable salt thereof in an amount of equivalent to ≥0.6 mg naloxone HCl dissolved in an application fluid of a volume≥200 µl. Particularly preferred can be the use of 0.6 mg naloxone HCl in an application fluid of a volume of 100 µl per dosing unit of the nasal spray. One application step comprising two consecutive administrations to the two nostrils would thus result in the provision of an amount of 1.2 mg naloxone HCl. Most preferred is an amount of equivalent to between about 0.65 mg naloxone HCl and 0.8 mg naloxone HCl or between about 1.3 mg naloxone HCl and about 1.6 mg naloxone HCl.

Alternatively, one may use 0.8 mg naloxone HCl in an application fluid of a volume of 100 µl per dosing unit of the nasal spray. One application step comprising two consecutive administrations to the two nostrils would thus result in the provision of an amount of 1.6 mg naloxone HCl. The nasal spray may in total comprise at least 600 µl which appears to be sufficient for at least five dosage units and residual volume needed e.g. for priming. Clearly, re-application for an initial titration or for application at later stages should be possible using such a spray.

Generally, the following volumes per dosing unit may particularly be used in the nasal spray according to the present invention: about 25 µl, about 50 µl, about 70 µl, about 90 µl, about 100 µl, about 120 µl, about 130 µl or about 140 µl.

Parameters describing the blood plasma curve can be obtained in clinical trials, first by once-off intranasal administration of the active agent naloxone to a number of test persons. The blood plasma values of the individual test persons are then averaged, e.g. a mean AUC, Cmax and tmax value is obtained. In the context of the present invention, pharmacokinetic parameters such as AUC, Cmax and tmax refer to mean values. Further, in the context of the present invention, in vivo parameters such as values for AUC, Cmax, tmax, refer to parameters or values obtained after administration of a single dose to human patients and/or healthy human subjects.

If pharmacokinetic parameters such as mean tmax, Cmax and AUC are measured for healthy human subjects, they are typically obtained by measuring the development of blood plasma values over time in a test population of approximately 10 to 25 healthy human subjects. Regulatory bodies such as the European Agency for the Evaluation of Medicinal Products (EMEA) or the Food and Drug Administration (FDA) will usually accept data obtained from e.g. 20 or 24 test persons. Preferably the parameters obtained relate to single dose administration studies.

The term "healthy" human subject in this context refers to a typical male or female of usually Caucasian origin with average values as regards height, weight and physiological parameters such as blood pressure etc. Healthy human subjects for the purposes of the present invention are selected according to inclusion and exclusion criteria which are based on and in accordance with recommendations of the International Conference for Harmonization of Clinical Trials (ICH). For the purposes of the present invention, healthy subjects may be identified according to the inclusion and exclusion criteria as outlined in the example section.

Further preferred embodiments of the present invention relate to:

1. An intranasal pharmaceutical dosage form comprising naloxone or a pharmaceutically acceptable salt thereof dissolved in an application fluid to a final concentration of between equivalent to 5 mg naloxone HCl per ml application fluid and 100 mg naloxone HCl per ml application fluid, preferably of between equivalent to 5 mg naloxone HCl per ml application fluid and 70 mg naloxone HCl per ml application fluid.
2. Dosage form according to 1, wherein a volume of between 200 µl and 50 µl of the application fluid, preferably a volume of 200 µl application fluid, more preferably a volume of 100 µl application fluid is administered per nostril.
3. Dosage form according to 1, wherein said final concentration is between equivalent to 6.5 mg naloxone HCl per ml application fluid and 33 mg naloxone HCl per ml application fluid.
4. Dosage form according to 3, wherein a volume of 200 µl application fluid, preferably of 100 µl application fluid, is administered per nostril.
5. Dosage form according to 1, wherein said final concentration is between equivalent to 8.5 mg naloxone HCl per ml application fluid and 44 mg naloxone HCl per ml application fluid.
6. Dosage form according to 5, wherein a volume of 150 µl application, preferably of 75 µl application fluid, is administered per nostril.
7. Dosage form according to 1, wherein said final concentration is between equivalent to 13 mg naloxone HCl per ml application fluid and 66 mg naloxone HCl per ml application fluid.
8. Dosage form according to 7, wherein a volume of 100 µl application fluid, preferably of 50 µl application fluid, is administered per nostril.
9. Dosage form according to 1, wherein said final concentration is between equivalent to 18.5 mg naloxone HCl per ml application fluid and 94 mg naloxone HCl per ml application fluid.
10. Dosage form according to 9, wherein a volume of 70 µl application fluid, preferably of 35 µl application fluid, is administered per nostril.
11. Dosage form according to any of 1 to 10, wherein said dosage form is for use in the treatment of opioid overdosing and/or at least one symptom thereof.

Still further preferred embodiments of the present invention relate to:

1. An intranasal pharmaceutical dosage form comprising a dosing unit comprising naloxone or a pharmaceutically acceptable salt thereof in an amount of equivalent to ≥0.5 mg naloxone HCl, preferably equivalent to ≥0.6 mg naloxone HCl, dissolved in an application fluid of a volume of ≤250 µl, preferably of a volume of ≥200 µl.
2. Dosage form according to 1, wherein the amount of naloxone or a pharmaceutically acceptable salt thereof is within a range of equivalent to 0.6 mg naloxone HCl to 12 mg naloxone HCl, preferably equivalent to 0.6 mg naloxone HCl to 6 mg naloxone HCl, more preferably equivalent to 0.6 mg naloxone HCl to 3.75 mg naloxone HCl, and most preferably equivalent to 0.6 mg naloxone HCl to 2.0 mg naloxone HCl.
3. Dosage form according to 1 or 2, wherein the volume of the application fluid is within a range of 200 µl to 35 µl, preferably of 200 µl to 50 µl, more preferably of 200 µl to 100 µl, and most preferably of 150 µl to 100 µl.
4. Dosage form according to any of 1 to 3, wherein the amount of naloxone or a pharmaceutically acceptable salt thereof is equivalent to 0.6 mg naloxone HCl or 1.2 mg naloxone HCl, and the volume of the application fluid is within a range of 200 µl to 50 µl, preferably of 200 µl to 100 µl, and more preferably of 150 µl to 100 µl.
5. Dosage form according to any of 1 to 4, wherein the dosage form provides for a bioavailability of the active agent naloxone in humans of 20% to 40% as determined against a reference of intravenously administered naloxone with a bioavailability set to 100%.
6. Dosage form according to any of 1 to 5, wherein the dosage form provides for an onset of action of the active agent naloxone in humans within 5 minutes to 18 minutes upon administration.
7. Dosage form according to any of 1 to 6, wherein the dosage form provides for a plasma half-live of the active agent naloxone in humans of 1.5 hours to 9 hours upon administration.
8. Dosage form according to any of 1 to 7, wherein the application fluid is selected from the group comprising water and an aqueous saline solution, preferably NaCl in water, more preferably NaCl in water to a concentration of 0.9% weight/volume.
9. Dosage form according to any of 1 to 8, wherein the dosage form comprises at least two dosage units, preferably at least three dosage units, more preferably at least four dosage units and most preferably at least five dosage units.
10. Dosage form according to any of 1 to 9, wherein the dosage form is selected from the group of dosage forms comprising a nasal spray, a nasal mucoadhesive dosage form and a Mucosal Atomizer Device.
11. Dosage form according to any of 1 to 10, wherein said dosage form is for use in the treatment of opioid overdosing and/or at least one symptom thereof.
12. Dosage form according to 12, wherein the opioid overdosing symptom is selected from the group comprising respiratory depression, altered level consciousness, miotic pupils, hypoxemia, acute lung injury and aspiration pneumonia.
13. Dosage form according to 11 or 12, wherein the dosage form is re-applied during an initial titration period in order to provide for an effective amount of naloxone.
14. Dosage form according to any one of 11 to 13, wherein the dosage form is combined with an intramuscular and/or intravenous dosage form comprising naloxone or a pharmaceutically acceptable salt thereof.
15. Use of naloxone or a pharmaceutically acceptable salt thereof in an amount of equivalent to ≥0.5 mg naloxone HCl dissolved in an application fluid of a volume of ≥250 μl in a dosing unit of an intranasal pharmaceutical dosage form.

EXAMPLES

Examples of embodiments of the present invention are outlined below. However, the examples should not be construed as limiting the scope of the present invention.

Example 1

In the following, the results of a single-center, open-label, randomized investigation in healthy volunteers to determine the intranasal and sublingual bioavailabilities of naloxone in a four-way crossover study are set out.

Summary of the Study

Objectives:

To assess the absolute bioavailability of 8 mg and 16 mg intranasally and 16 mg sublingually administered naloxone compared with 1 mg of intravenously administered naloxone to healthy subjects.

Methodology:

A single-center, open-label, randomized, 4-way crossover study using 8 mg and 16 mg intranasally, 16 mg naloxone sublingually, and 1 mg intravenous naloxone. A 4-sequence Williams design was used.

Number of Subjects:

Planned: 12 subjects; full analysis for PK metrics: 12 subjects; Safety population: 12 subjects; Completed: 10 subjects; Discontinued: 2 subjects [due to their own choice].

Indication and Criteria for Inclusion:

Subjects were males and/or females aged ≥18 and ≤55 years who were in good health as determined by no clinically significant findings in medical history, physical examination (including nasopharyngeal and oral cavity), electrocardiograms (ECGs), and clinical laboratory determinations.

Test Treatment, Dose, and Mode of Administration:

1. Naloxone 8 mg and 16 mg were administered as 400 μl intranasally (200 μl per nostril). This corresponded to approximately 0.11 mg/kg bodyweight (for 8 mg) and 0.22 mg/kg bodyweight (for 16 mg).

The administration was as follows:

The pump of the nasal spray was primed by removing the cap and pressing downward. This is repeated at least 6 times or until a fine spray appears; priming is done just prior to dosing.

The subject is in a standing or upright position and should gently blow the nose to clear the nostrils. The subject should tilt the head forward slightly and gently close one nostril by pressing the outside of the nose with a finger on the nostril to be closed.

The device is inserted into the open nostril and it is sprayed 2 times into the nostril.

The subject should gently breath inward through the nostril, the device is removed, and the steps are repeated for the other nostril.

2: Naloxone 16 mg was administered sublingually in a 1 ml solution which was retained under the tongue for 5 minutes.

Naloxone hydrochloride powder was obtained from Mallenckrodt Chemical (Lot no. E09611). Solutions were prepared in 0.9% sodium chloride solution (pH adjusted to 5.6).

Reference Treatment, Dose, and Mode of Administration:

Intravenous naloxone 1 mg administered as a 1 ml bolus over a 30-second period. Naloxone hydrochloride 1 mg/ml in 10 ml vials was obtained from Bristol-Meyers Squibb Holdings Pharma, Ltd, USA.

Duration of Treatment and Study:

The screening period occurred within 14 days prior to dosing in Period 1. There were 4 single-dose, open-label treatments, with a minimum 14-day washout between each treatment. Subjects had an End-of-Study medical evaluation after assessments for the fourth dosing were complete on Day 45, or upon early study discontinuation (see FIG. 1).

Treatment Schedule:

Single dose of study drug in each of 4 study periods; each dose of study drug followed by at least a 14-day washout period (Periods 1, 2 and 3 only).

Criteria for Evaluation:

Analysis Populations:

The enrolled population was defined as any subject who signed an Informed Consent Form. The safety population was defined as any subject who received any study treatment and had at least one subsequent safety assessment. The full analysis population for pharmacokinetic metrics was defined as those subjects who received a study treatment and had at least one subsequent valid PK metric.

Pharmacokinetic/Blood Sampling Times:

Blood sampling for pharmacokinetics was performed at the following times relative to each dose: time 0 (just prior to dosing), Minutes 1, 2, 4, 10, 30, 40 and Hours 1, 2, 4, 6, 8, 12, 16, 24.

Pharmacokinetic Metrics:

Individual subject pharmacokinetic metrics for naloxone and 6β-naloxol AUCt, AUCINF, Cmax, tmax, Lambdaz and t½z were derived using noncompartmental methods by a validated pharmacokinetic analysis program.

Safety:

Safety was assessed using adverse events, clinical laboratory results, vital signs, and ECGs.

Bioanalytical Methods:

Plasma concentrations of naloxone and 6β-naloxol were quantified by LC-MS/MS methodology using a previously validated assay. Additionally, subject plasma samples were assayed (via GLP and/or non-GLP methods) for other relevant naloxone metabolites.

Statistical Methods:

Plasma concentrations and pharmacokinetic metrics were summarized descriptively (n, mean, SD, geometric mean where appropriate for AUCt, AUCINF and Cmax, SE (for concentrations only), median, minimum and maximum were determined) for each analyte for each treatment. Absolute bioavailabilities of the intranasal and sublingual treatments were calculated.

Details of the Study

Study Design:

The study was a single-dose, open-label, 4-treatment, 4-period, randomized, crossover study in healthy adult male and female subjects in order to assess the pharmacokinetics of two doses of nasally administered and one dose of sublingually administered naloxone compared with intravenously administered naloxone. Subjects received each of the 4 treatments according to a random code, with at least a 14-day washout period between each dosing. Subjects were screened within 14 days before the first dosing day. Eligible subjects then checked in to the study unit on the evening before dosing in each study period. Subjects were administered the study drug the next morning, following an overnight fast. Pharmacokinetic blood samples were taken for 36 hours after administration of study drug in each study period, and subjects were discharged after the 24-hour blood sample. Subjects returned to the study unit to provide the 36-hr PK blood sample. Throughout the study, vital signs were monitored and adverse events (AEs) recorded. Subjects underwent end-of-study procedures, similar to those at screening, during their final outpatient visit or upon early termination/discontinuation from the study.

Inclusion Criteria for Study Population:

Males and females of any ethnic group.

Ages≥18 and ≤55 years inclusive.

BMI within the range 18-32 kg/m$^2$ inclusive and within the weight range 50-100 kg inclusive.

Females must be nonlactating, nonpregnant, and provide a negative serum pregnancy test at screening and a negative urine pregnancy test within 24 hours before receiving each dose of the study drug. WOCBP must agree to use a hormonal contraceptive, barrier contraceptive with additional spermicide, or an intrauterine device. Female subjects who are postmenopausal must have been postmenopausal for >1 year and have elevated serum FSH consistent with postmenopausal status.

Generally of good health, evidenced by a lack of significantly abnormal findings on medical history, physical examination, clinical laboratory tests, vital signs, and ECGs.

Provide written informed consent. If HIPAA criteria are not incorporated into the consent form, a separate addendum to the informed consent form must be signed.

Willing and able to follow all rules of the protocol, including returning for outpatient visits.

Exclusion Criteria for Study Population:

Any history of hypersensitivity to naloxone or related compounds.

Subjects who meet American Academy of Pain Medicine, the American Pain Society, and American Society of Addiction Medicine criteria for addiction: "characterized by behaviors that include one or more of the following: Impaired control over drug use, compulsive use, continued use despite harm, and craving," but for this study not including tobacco dependence.

OOWSL4 score>4 within 1 hour prior to dosing.

History of or any current conditions that might interfere with drug absorption, distribution, metabolism, and/or excretion.

Conditions of the nose that might interfere with intranasal drug absorption, including any type of rhinitis, polyps, complete or partial obstruction of any etiology (e.g., significant deviation of nasal septum, recent trauma or surgery), active bleeding or recent history of recurrent nose bleeds, or any ulcerations.

Any foreign object (including jewelry) in the nasal or oral cavities or any perforation into either cavity or through the septum or tongue (including piercings for jewelry).

Abnormal mucosa on nasal speculum examination including: Atrophic mucosa, perforations, multiple polyps, fully obstructed nasal passage on either side, hemangioma Conditions of the mouth that might interfere with intraoral (sublingual) drug absorption, including any type of ulceration, infection, or recent trauma or surgery. Routine dental cleaning within the previous two weeks or planned dental cleaning during the study.

Poor oral hygiene, including gingivitis.

Abnormal oral mucosa on examination including:

atrophic mucosa, malignant or benign tumors (including fibromas and hemangiomas) or cysts, bullous lesions (eg, pemphigus or erythema multiforme), glossitis, aphthous ulcers, lichen planus, leukoplakia, infections [bacterial, mycotic, viral (eg, herpetic)] Any use of intranasal products (prescription, nonprescription, or anything else administered intranasally) within 4 weeks prior to dosing.

Use of any prescription drugs (except hormone replacement therapy (HRT) for postmenopausal females, or contraceptive medications) within 4 weeks prior to first dosing or during the course of the study. Exceptions may be made on a case-by-case basis for drugs with a short half-life (eg, tetracycline) and/or no known significant drug interactions (eg, finasteride).

Use of any nonprescription medications, including vitamins and herbal or mineral supplements, during the 7 days preceding or 2 days following any dosing. Exceptions may be made on a case-by-case basis for medications with a short half-life.

Participation in a clinical drug study during the 30 days preceding the initial dose in this study.

Any significant illness within 4 weeks prior to the first dosing.

Donation of blood or blood products within 30 days prior to study drug administration or anytime during the study.

Refusal to abstain from food at least 10 hours preceding and 4 hours following study drug administration or refusal to abstain from caffeine- or xanthine-containing beverages entirely during each confinement.

Alcohol intake exceeding the equivalent to >21 units/ week (12 oz beer=4 oz wine=1.5 oz shot=1 unit).

Consumption of alcoholic beverages within 48 hours of study drug administration.

History of smoking within 45 days of study drug administration (must have a negative urine cotinine at screening).

Positive results at screening of urine drug screen, blood alcohol, or serology, including anti-HBc and anti-HCV.

the Investigator believes the subject to be unsuitable for some reason not specifically stated in the exclusion criteria.

Method of Administration:

Subjects were administered the study medication on the mornings of each dosing day. Subjects were dosed following an overnight fast of at least 10 hours. After the dosing, subjects remained in an upright sitting position for a minimum of 4 hours. The intranasal doses were administered via a metered dose nasal spray device. 200 µl per nostril were administered for a total volume of 400 µl. For each intranasal administration, the head was tilted slightly forward. Subjects were instructed to refrain from blowing the nose or sneezing after administration. Subjects who receive intranasal dosing documented any sneezes that occurred within 5 minutes of dosing in the source documents.

The sublingual dose of naloxone was administered by having the subject retain the solution (0.4 ml) under the tongue for 5 minutes, after which the mouth was thoroughly rinsed with water and the expectorated rinse residue discarded. Subjects were in a standing or upright sitting position. Subjects were instructed not to swallow any of the rinse. They also refrained from drinking water for 1 hour after the rinse. Intravenous naloxone will be given as a 30-second bolus while the subject is sitting.

Results:

Safety:

The incidence of treatment-emergent adverse events (TE-AEs) was similar across all treatment groups: 8 mg intranasal naloxone [3 TEAEs]; 16 mg intranasal naloxone [5 TEAEs]; 16 mg sublingual naloxone [1 TEAE]; 1 mg intravenous naloxone [4 TEAEs]. The most common TEAEs occurred in the Gastrointestinal Disorders and Nervous System Disorder SOCs (System Organ Class).

Gastrointestinal Disorders TEAEs were observed in the 16 mg intranasal, 1 mg intravenous, and 16 mg sublingual groups only, whereas Nervous System TEAEs were observed in the 8 mg and 16 mg intranasal and 1 mg intravenous groups only.

There were no deaths, serious adverse events, or other significant adverse events.

One subject recorded a markedly abnormal high triglyceride value (8.355 mmol/l) on Day 44 of the study. However, the subject had recorded a triglyceride value above the normal range (4.189 mmol/l) on Day −9, prior to receiving study drug.

Another subject reported a markedly abnormal low potassium value (3.3 mmol/l), a markedly abnormal high SGPT value (371 U/l), and a markedly abnormal high total bilirubin value (39.33 umol/l) on Day 44 of the study. Potassium, SGPT, and total bilirubin values for this subject were normal prior to the subject receiving study drug. These laboratory findings were observed during the routine lab evaluation and not reported as suspected adverse events by the investigator. Therefore, a causality assessment was not provided. Due to the timely relationship to the administration of the investigated drug the sponsor rated the event to be "possibly" related according to the WHO algorithm.

No clinically relevant changes in ECG occurred.

Three subjects had markedly abnormal changes in pulse rate and one subject had a markedly abnormal change in blood pressure. TEAEs of vasovagal attack were reported in 3 subjects after intranasal application of naloxone (2 subjects: one subject after 8 mg and one subject after 16 mg) and intravenous bolus (1 mg) administration (1 subject). No overall trend in abnormal vital sign changes was observed in this study.

Concomitant therapy was administered to 6 subjects for 10 TEAEs. Three of these 10 TEAEs were vasovagal attacks and subjects were placed in the supine position to recover. No additional medication was given to these subjects. One subject received additional medication for headache twice. Additional medication was administered for single events of hemorrhoid removal, urticaria, gastroesophageal reflux, nausea and urinary tract infection.

Pharmacokinetic:

Following intranasal administration of naloxone there was a very early appearance of the drug in the systemic circulation, with peak plasma concentrations being attained as early as 6 minutes (median 18 minutes) after dosing. Mean absolute bioavailabilities of 32% and 27% were recorded from the 8 mg and 16 mg doses respectively, by dividing the AUC of the intranasal naloxone by the AUC of the intravenous reference naloxone and multiplying by 100%. In contrast to the rapid elimination half life associated with the intravenous reference (<1 h), mean half lives of several hours were recorded from the 8 mg and 16 mg intranasal doses, respectively. These data indicate a substantial level of absorption of naloxone by the intranasal route coupled with a reasonably slow elimination pattern. In contrast, the mean absolute bioavailability of naloxone when administered by the sublingual route was approximately 2% versus the intravenous reference. This is comparable to that recorded previously following oral administration.

The mean pharmacokinetic parameters for naloxone are depicted in FIG. 2.

Example 2

Based on the data gained in Example 1, the following predictions of amounts of naloxone administered intravenously or intranasally were carried out.

A typical starting point for an intravenous administration of naloxone is in the range of about 0.4 mg (IV). Based on the AUC-values for 1 mg IV naloxone, 8 mg IN naloxone and 16 mg IN of example 1, it can be estimated that the range of dose-proportionality to 1 mg IV is in the range of 3 mg to 4 mg for IN naloxone. For 0.4 mg IV naloxone, this results in typical starting amounts for naloxone administered intranasally ranging from 1.2 mg to 1.6 mg.

Based on the original data of the study of example 1 on either 8 mg naloxone or 16 mg naloxone administered intranasally (IN) and of 1 mg naloxone administered intravenously (IV), plasma concentrations were predicted for the following amounts: 0.4 mg naloxone IV, 1.2 mg naloxone IN and 1.6 mg naloxone IN.

Using a first method (Excel), the Cmax and AUCt-values based on the original data for the 8 mg naloxone administered IN and the 1 mg naloxone IV were calculated by performing non-compartmental analysis on the mean profiles which had been scaled to the proposed doses with the following results:

|  | Cmax (pg/ml) | AUCt (pg · h/ml) |
| --- | --- | --- |
| 1.2 mg IN | 1535.2 | 3159.6 |
| 1.6 mg IN | 2046.9 | 4212.8 |
| 0.4 mg IV | 4735.2 | 4578.9 |

Figure 3:
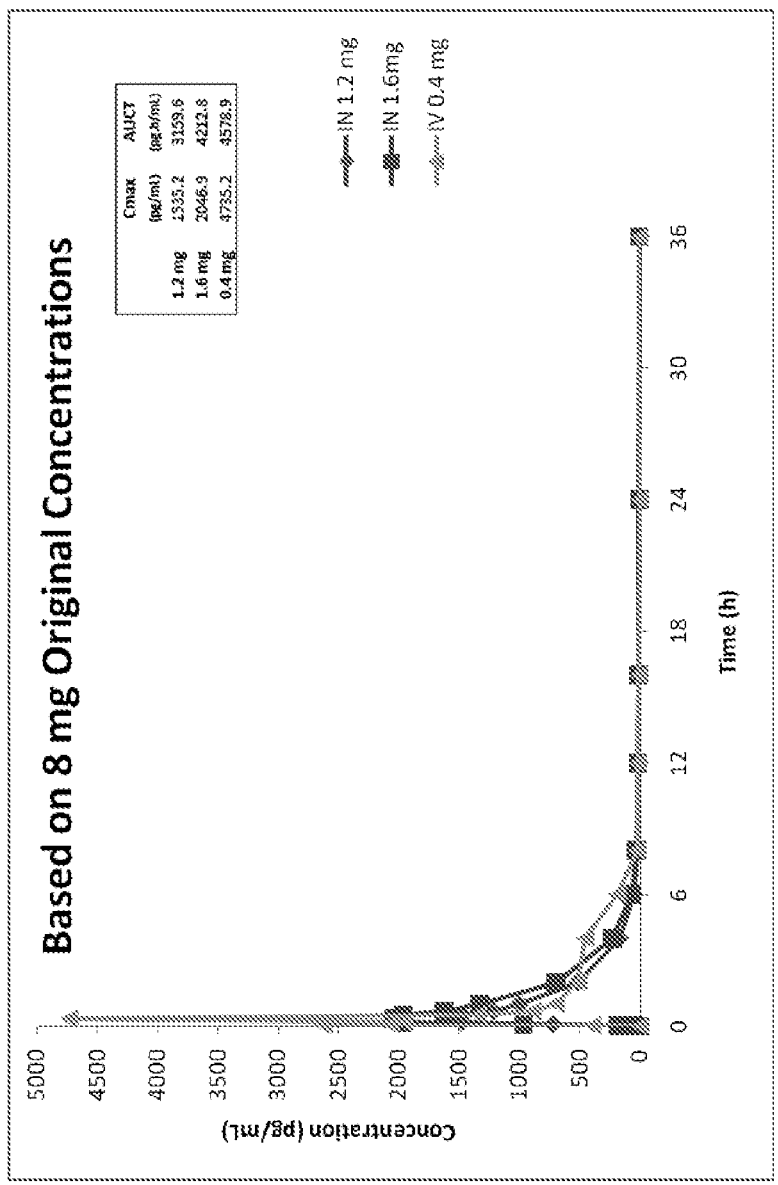
FIG. 3 shows the estimated curves (based on the data of Example 1: 8 mg naloxone HCl applied intranasally) using Excel for 0.4 mg naloxone applied intravenously (IV), 1.2 mg naloxone applied intranasally (IN) and 1.6 mg naloxone applied IN for a period of 36 hours.
Figure 4:
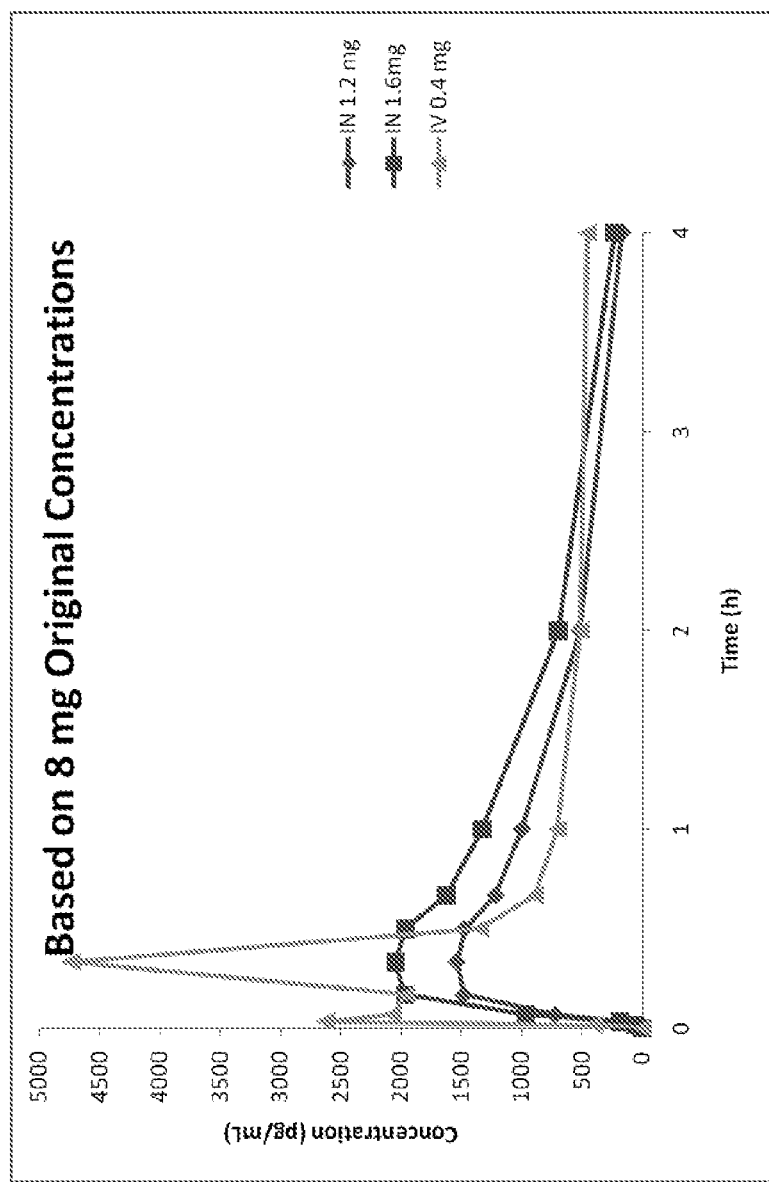
FIG. 4 shows the estimated curves (based on the data of Example 1: 8 mg naloxone HCl applied intranasally) using Excel for 0.4 mg naloxone applied intravenously (IV), 1.2 mg naloxone applied intranasally (IN) and 1.6 mg naloxone applied IN for a period of 4 hours.

The corresponding curves are depicted in FIG. 3 (for the total time period of 36 h) and in FIG. 4 (for a time period of 4 h).

Using Excel, the Cmax and AUCt-values based on the original data for the 16 mg naloxone administered IN and the 1 mg naloxone administered IV were also calculated by performing non-compartmental analysis on the mean profiles which had been scaled to the proposed doses with the following results:

|  | Cmax (pg/ml) | AUCt (pg · h/ml) |
| --- | --- | --- |
| 1.2 mg IN | 1052.5 | 2585.0 |
| 1.6 mg IN | 1403.4 | 3446.7 |
| 0.4 mg IV | 4735.2 | 4578.9 |

Figure 5:
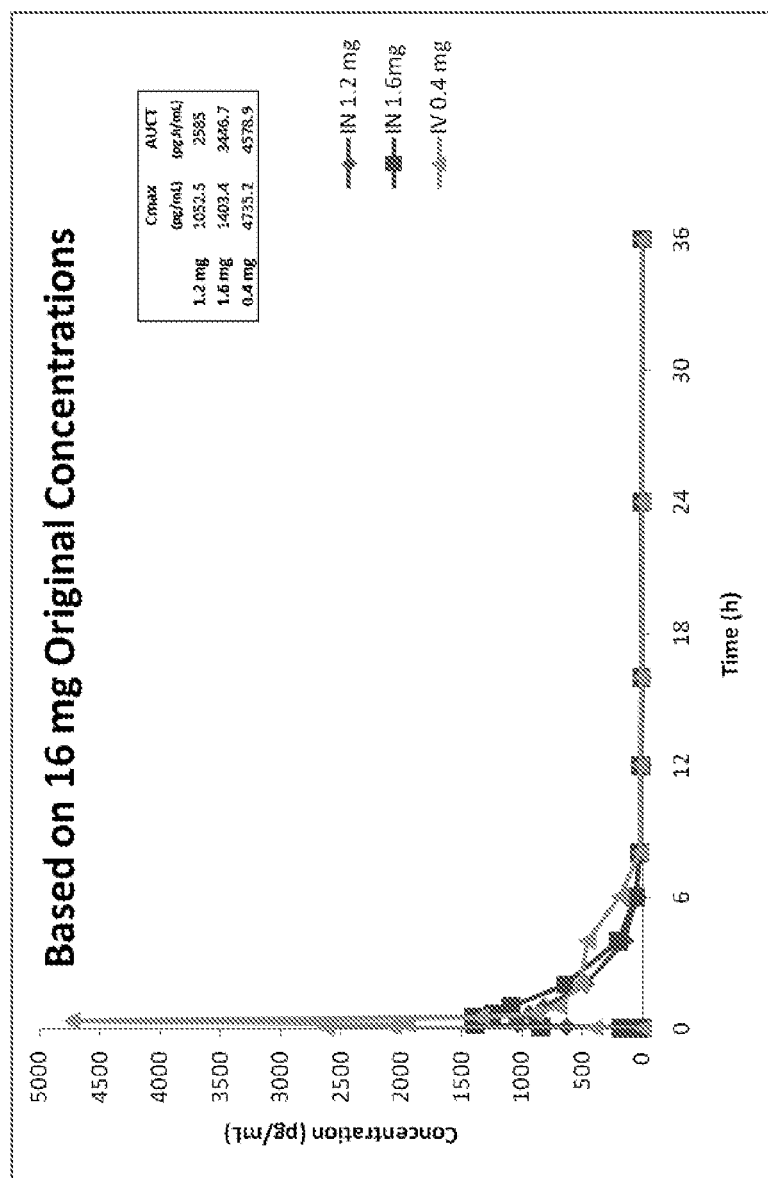
FIG. 5 shows the estimated curves (based on the data of Example 1: 16 mg naloxone HCl applied intranasally) using Excel for 0.4 mg naloxone applied intravenously (IV), 1.2 mg naloxone applied intranasally (IN) and 1.6 mg naloxone applied IN for a period of 36 hours.
Figure 6:
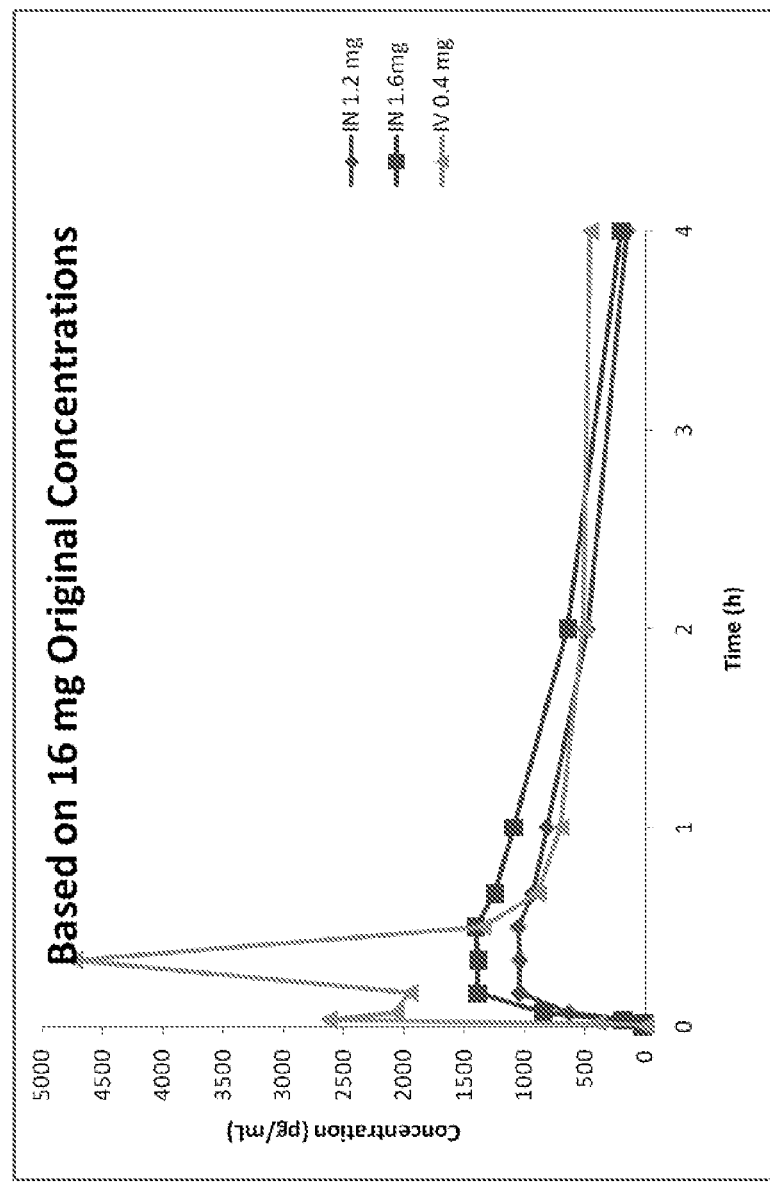
FIG. 6 shows the estimated curves (based on the data of Example 1: 16 mg naloxone HCl applied intranasally) using Excel for 0.4 mg naloxone applied intravenously (IV), 1.2 mg naloxone applied intranasally (IN) and 1.6 mg naloxone applied IN for a period of 4 hours.

The corresponding curves are depicted in FIG. 5 (for the total time period of 36 h) and in FIG. 6 (for a time period of 4 h).

Using a second method (WinNonlin Modeling), the original data for the 8 mg naloxone administered IN were fitted by a compartmental pharmacokinetic model followed by the simulations of the concentrations based on the model. The corresponding Cmax and AUCt-values are as follows (for the total time period of 36 h):

|  | Cmax (pg/ml) | AUCt (pg · h/ml) |
| --- | --- | --- |
| 1.2 mg IN | 1599.5 | 2876.2 |
| 1.6 mg IN | 2132.6 | 3835.0 |

Figure 7:
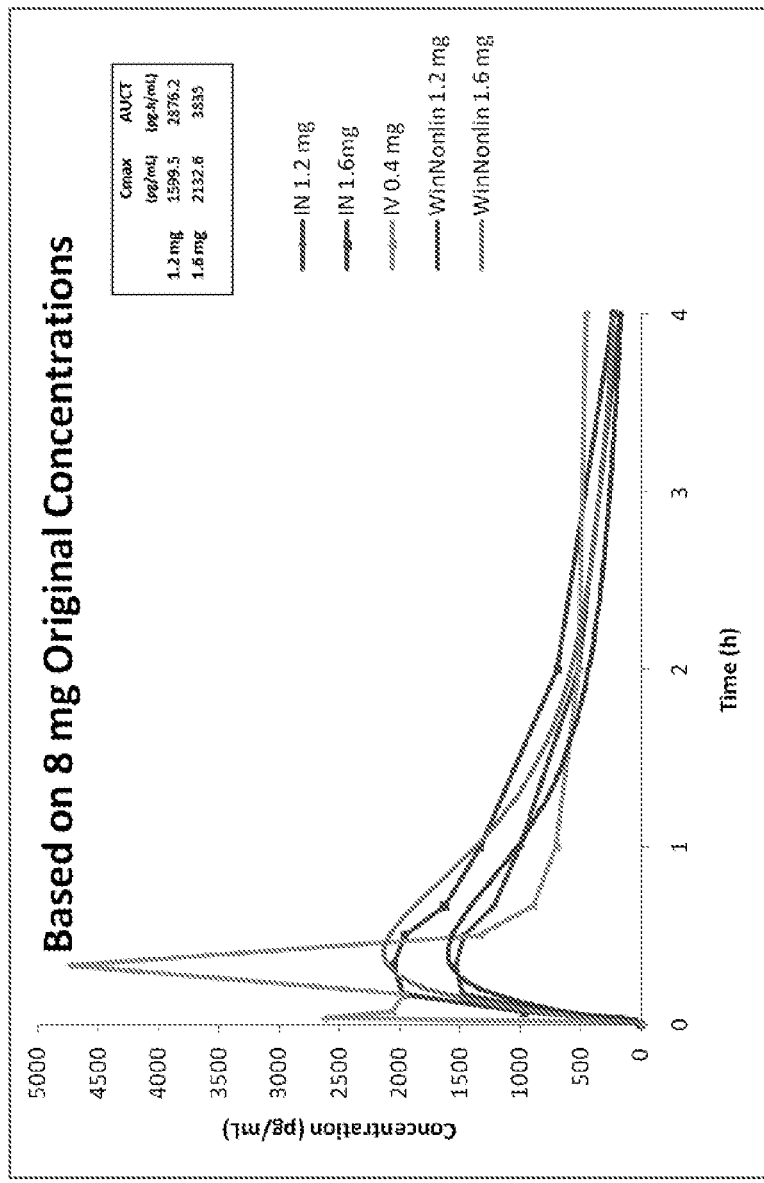
FIG. 7 shows the estimated curves (based on the data of Example 1: 8 mg naloxone HCl applied intranasally) using either Excel or WinNonlin for 0.4 mg naloxone applied intravenously (IV, Excel only), 1.2 mg naloxone applied intranasally (IN) and 1.6 mg naloxone applied IN for a period of 4 hours.

The corresponding curves are depicted in FIG. 7 for a time period of 4 h together with the predicted concentrations using Excel (see above).

Using WinNonlin, the original data for the 16 mg naloxone administered IN were also fitted by a compartmental pharmacokinetic model followed by the simulations of the concentrations based on the model. The corresponding Cmax and AUCt-values are as follows (for the total time period of 36 h):

|  | Cmax (pg/ml) | AUCt (pg · h/ml) |
|---|---|---|
| 1.2 mg IN | 893.5 | 2163.1 |
| 1.6 mg IN | 1191.3 | 2884.1 |

Figure 8:
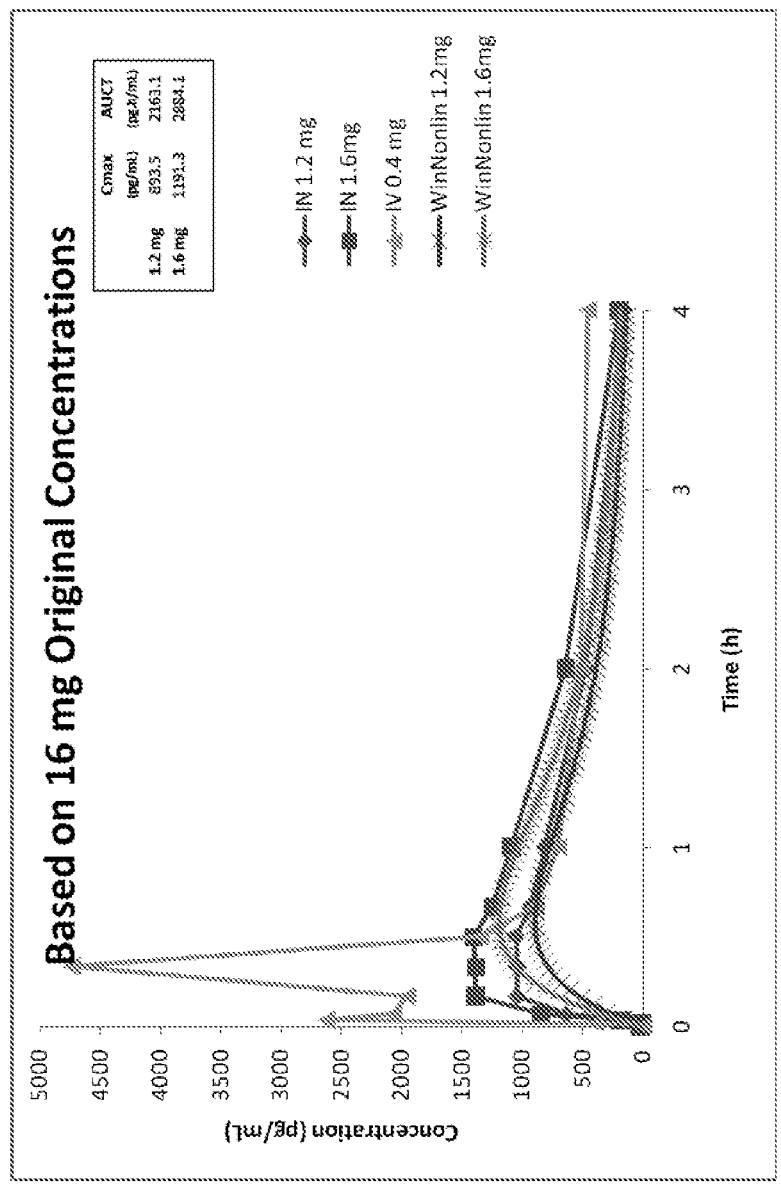
FIG. 8 shows the estimated curves (based on the data of Example 1: 16 mg naloxone HCl applied intranasally) using either Excel or WinNonlin for 0.4 mg naloxone applied intravenously (IV, Excel only), 1.2 mg naloxone applied intranasally (IN) and 1.6 mg naloxone applied IN for a period of 4 hours.

The corresponding curves are depicted in FIG. 8 for a time period of 4 h together with the predicted concentrations using Excel (see above).

As can particularly be derived from FIG. 7, the IN naloxone plasma levels predicted for amounts of 1.2 mg and 1.6 mg, respectively, display a smoother increase with a longer plateau compared to IV administration of 0.4 mg. However, the initial slope of the IN-curves is rather steep as well. Further, the IN-curves display a rather smooth decline following Cmax compared to the IV curve.

Example 3

As evident particularly from FIGS. 4, 6, 7 and 8, the plasma concentration curve predicted for an amount of 0.4 mg naloxone IV displays two peaks, wherein the first peak after a few minutes is followed by a second peak corresponding to the Cmax-peak.

Due to this rather unusual IV profile, it was decided to exclude one outlying subject who was apparently responsible for the "double peak IV profile" when predicting the plasma concentration curve for an amount of 0.4 mg naloxone administered intravenously. The calculations using Excel and WinNonlin for the 1.2 mg naloxone IN and 1.6 mg naloxone IN correspond to the data as shown in Example 2.

Using Excel, the Cmax and AUCt-values based on the 1 mg naloxone IV data excluding the outlying subject were calculated by performing non-compartmental analysis on the mean profiles which had been scaled to the dose of 0.4 mg IV with the following results (depicted again with the IN-values based on the 8 mg IN data):

|  | Cmax (pg/ml) | AUCt (pg · h/ml) |
|---|---|---|
| 1.2 mg IN | 1535.2 | 3159.6 |
| 1.6 mg IN | 2046.9 | 4212.8 |
| 0.4 mg IV | 2881.7 | 3812.2 |

Figure 9:
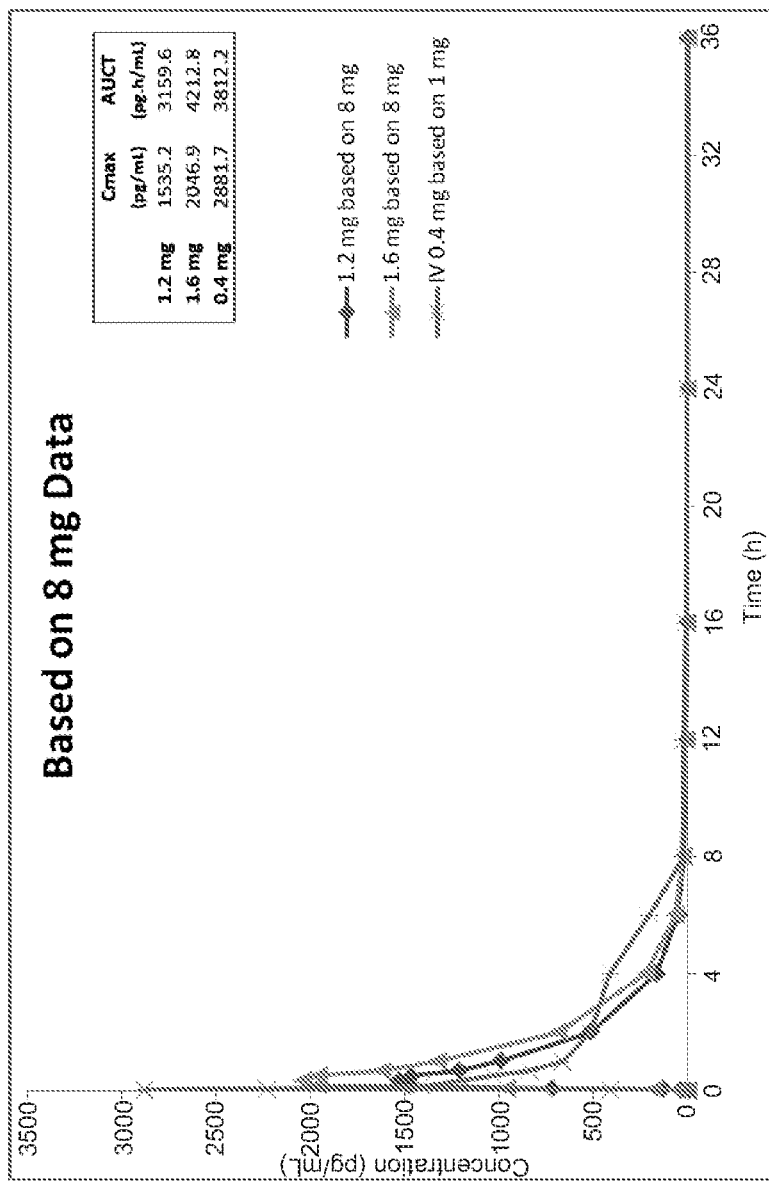
FIG. 9 shows the estimated curves (based on the data of Example 1: 8 mg naloxone HCl applied intranasally) using Excel for 0.4 mg naloxone applied intravenously (IV) [wherein, compared to FIG. 3, one outlying subject was excluded], 1.2 mg naloxone applied intranasally (IN) and 1.6 mg naloxone applied IN for a period of 36 hours.
Figure 10:
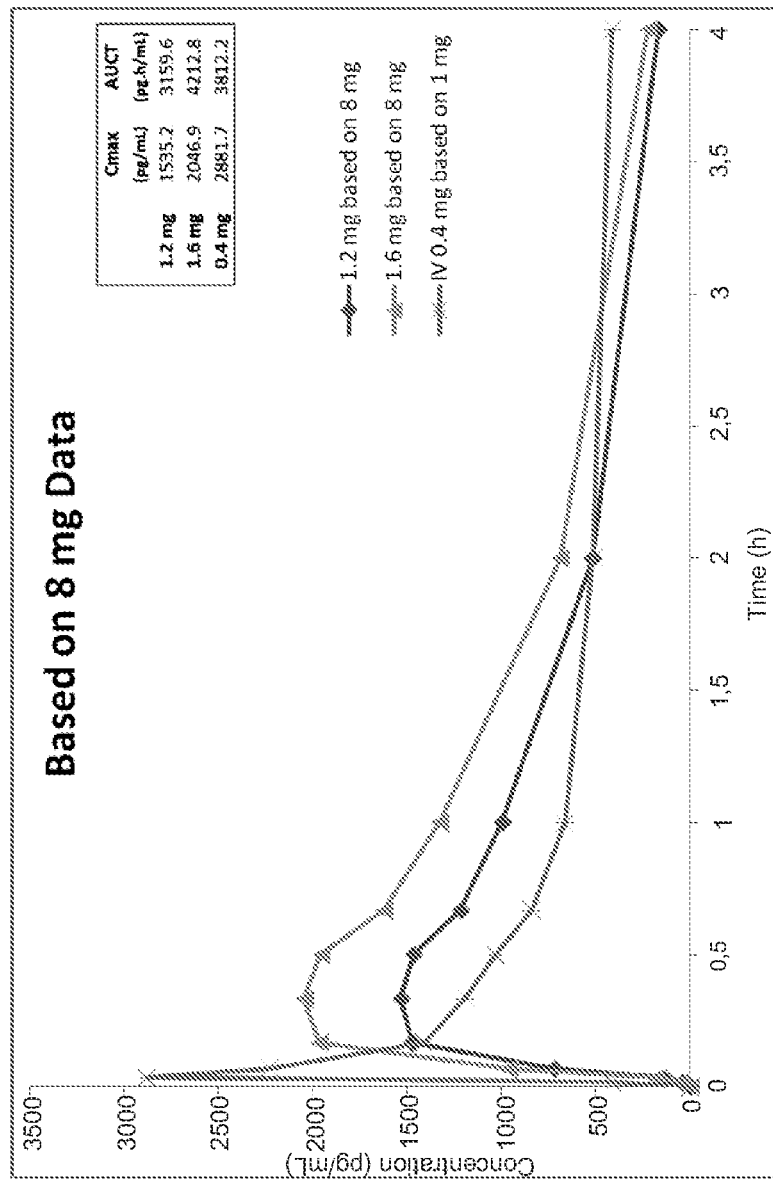
FIG. 10 shows the estimated curves (based on the data of Example 1: 8 mg naloxone HCl applied intranasally) using Excel for 0.4 mg naloxone applied intravenously (IV) [wherein, compared to FIG. 4, one outlying subject was excluded], 1.2 mg naloxone applied intranasally (IN) and 1.6 mg naloxone applied IN for a period of 4 hours.

The corresponding curves are depicted in FIG. 9 (for the total time period of 36 h) and in FIG. 10 (for a time period of 4 h).

In the following table, the values calculated for Cmax and AUCt based on the 1 mg naloxone IV data excluding the outlying subject are shown in comparison to the Cmax and AUCt-values calculated for 1.2 mg IN and 1.6 mg IN based on the 16 mg IN data:

|  | Cmax (pg/ml) | AUCt (pg · h/ml) |
|---|---|---|
| 1.2 mg IN | 1052.5 | 2585.0 |
| 1.6 mg IN | 1403.4 | 3446.7 |
| 0.4 mg IV | 2881.7 | 3812.2 |

Figure 11:
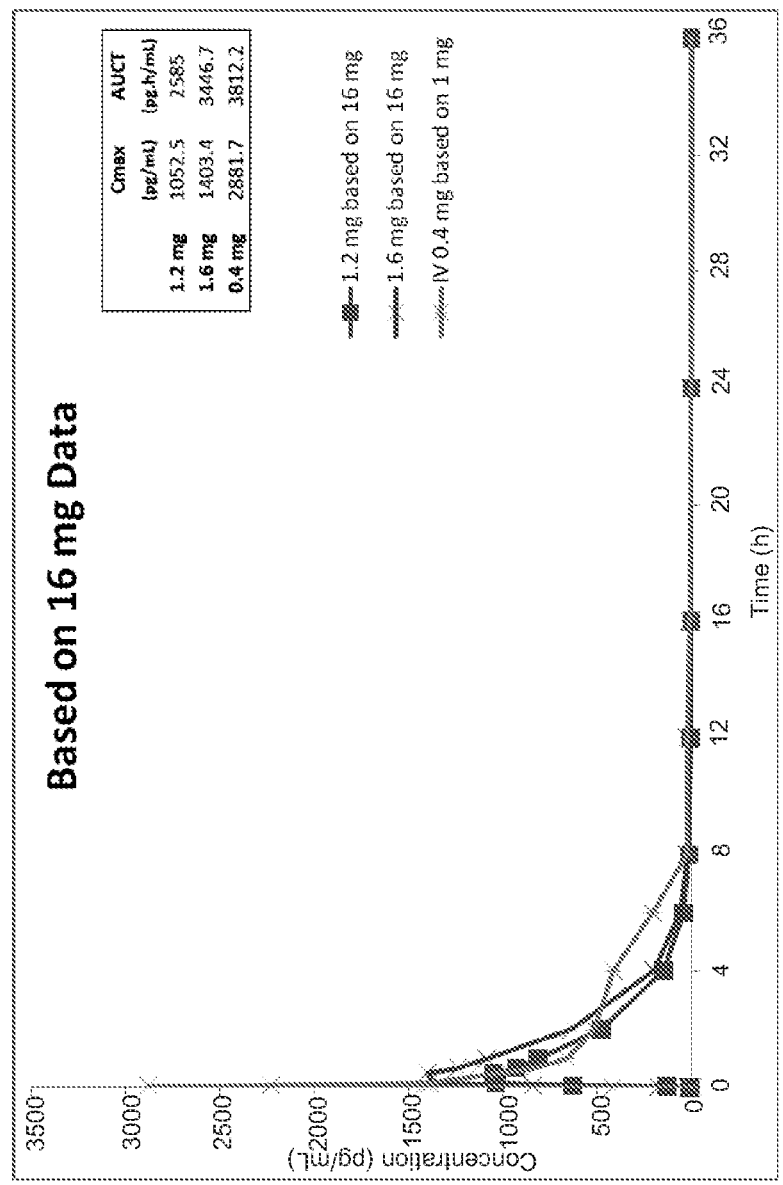
FIG. 11 shows the estimated curves (based on the data of Example 1: 16 mg naloxone HCl applied intranasally) using Excel for 0.4 mg naloxone applied intravenously (IV) [wherein, compared to FIG. 5, one outlying subject was excluded], 1.2 mg naloxone applied intranasally (IN) and 1.6 mg naloxone applied IN for a period of 36 hours.
Figure 12:
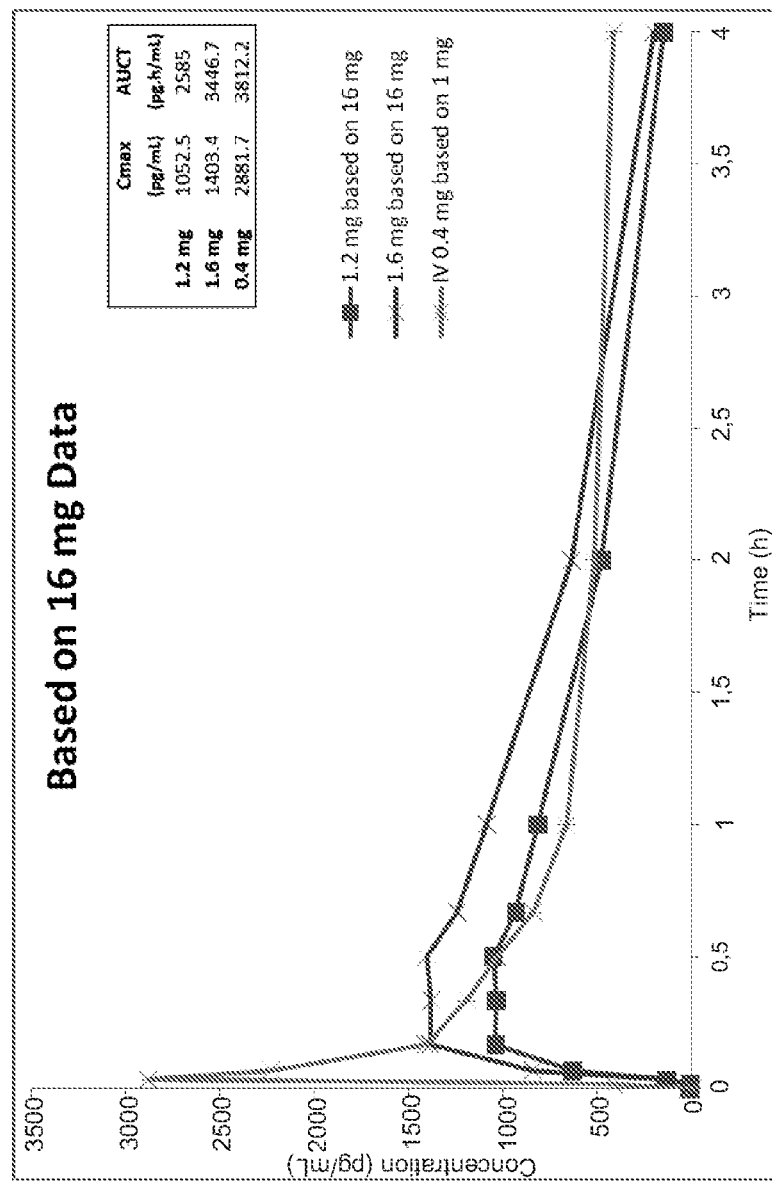
FIG. 12 shows the estimated curves (based on the data of Example 1: 16 mg naloxone HCl applied intranasally) using Excel for 0.4 mg naloxone applied intravenously (IV) [wherein, compared to FIG. 6, one outlying subject was excluded], 1.2 mg naloxone applied intranasally (IN) and 1.6 mg naloxone applied IN for a period of 4 hours.

The corresponding curves are depicted in FIG. 11 (for the total time period of 36 h) and in FIG. 12 (for a time period of 4 h).

Figure 13:
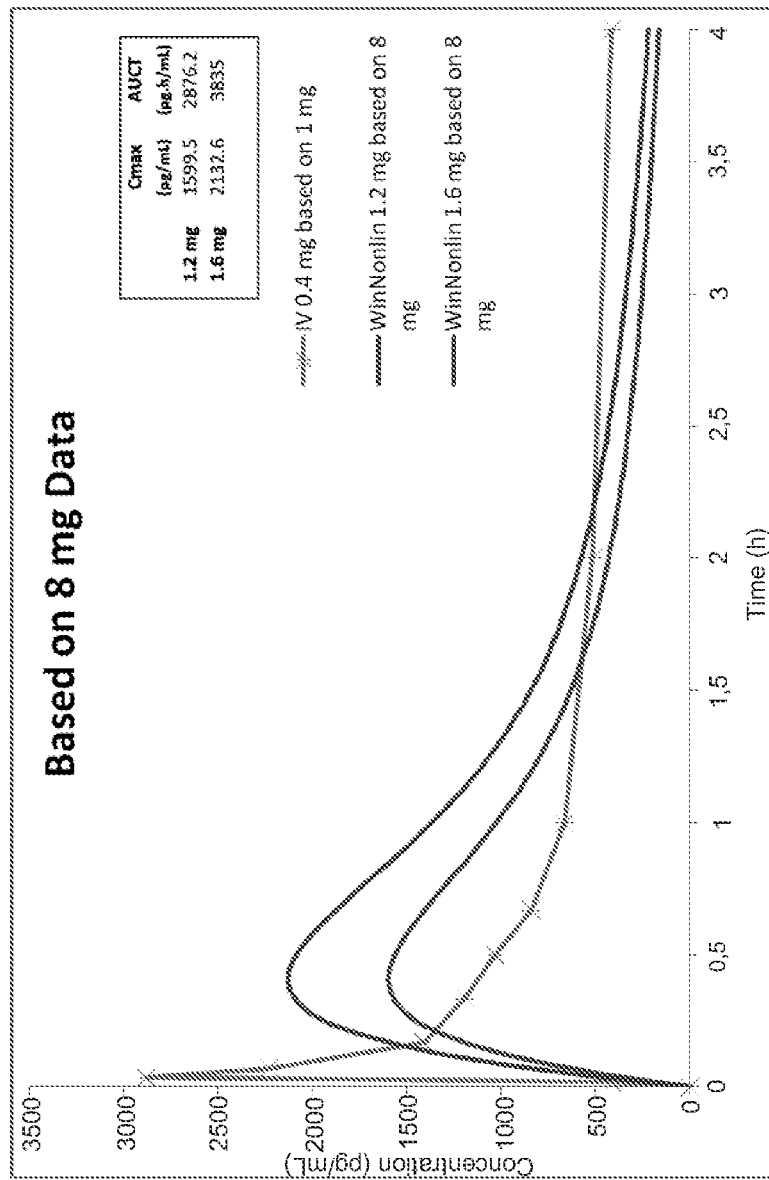
FIG. 13 shows the estimated curves (based on the data of Example 1: 8 mg naloxone HCl applied intranasally) using WinNonlin for 1.2 mg naloxone applied intranasally (IN) and 1.6 mg naloxone applied IN as well as for 0.4 mg naloxone applied intravenously (IV, using Excel [wherein, compared to FIG. 7, one outlying subject was excluded]) for a period of 4 hours.
Figure 14:
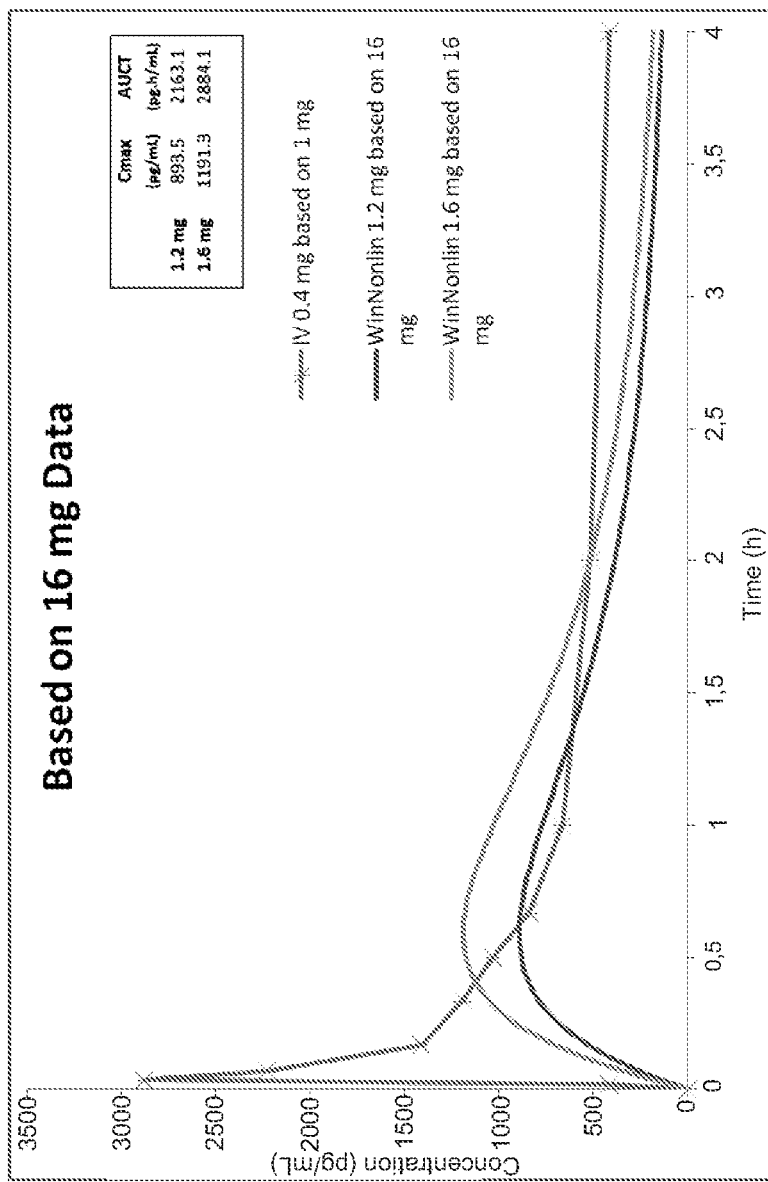
FIG. 14 shows the estimated curves (based on the data of Example 1: 16 mg naloxone HCl applied intranasally) using WinNonlin for 1.2 mg naloxone applied intranasally (IN) and 1.6 mg naloxone applied IN as well as for 0.4 mg naloxone applied intravenously (IV, using Excel [wherein, compared to FIG. 8, one outlying subject was excluded]) for a period of 4 hours.

As already described in example 2, the original data for the 8 mg naloxone administered IN were also fitted by a compartmental pharmacokinetic model followed by the simulations of the concentrations based on the model (WinNonlin Modeling). The corresponding curves together with the 0.4 mg IV curve excluding the outlying subject (based on Excel) are depicted in FIG. 13 for a time period of 4 h. FIG. 14 shows the corresponding curves for the modeling based on the 16 mg naloxone IN data together with the 0.4 mg IV curve excluding the outlying subject (based on Excel).

Figure 15:
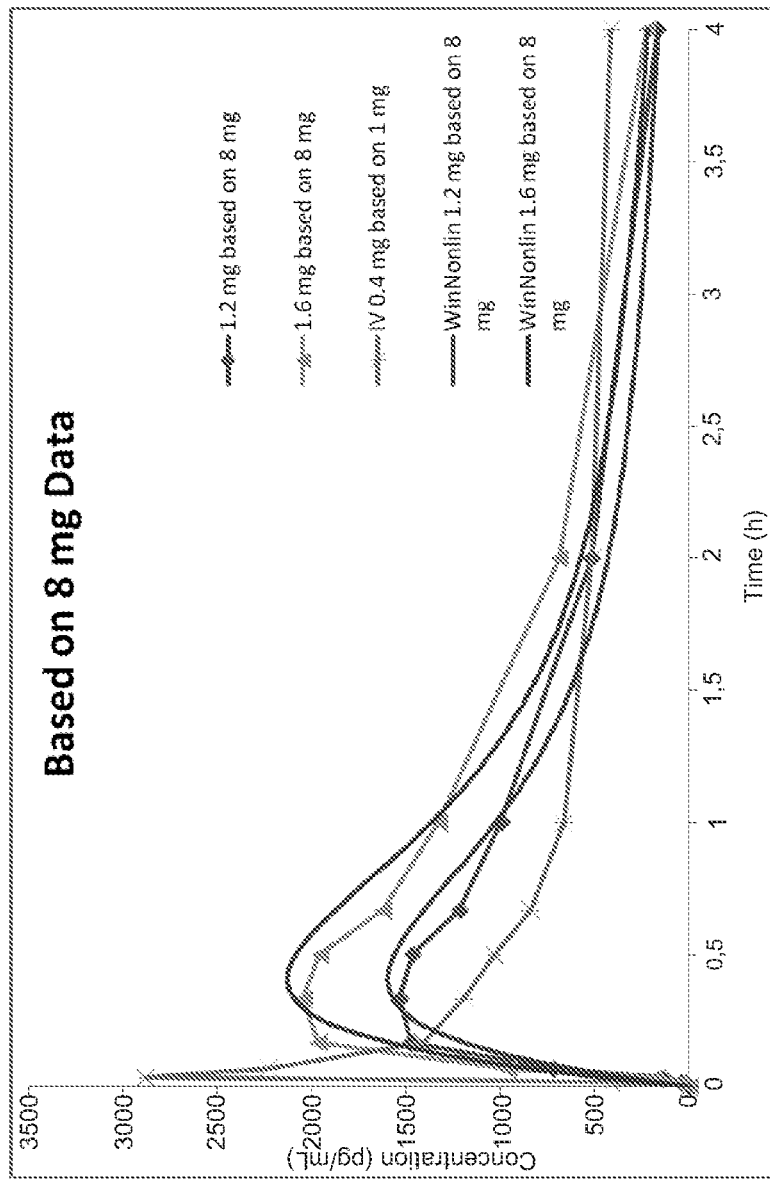
FIG. 15 shows the estimated curves (based on the data of Example 1: 8 mg naloxone HCl applied intranasally) using either Excel or WinNonlin for 1.2 mg naloxone applied intranasally (IN) and 1.6 mg naloxone applied IN for a period of 4 hours as well as for 0.4 mg naloxone applied intravenously (IV, using Excel [wherein, compared to FIG. 7, one outlying subject was excluded]).
Figure 16:
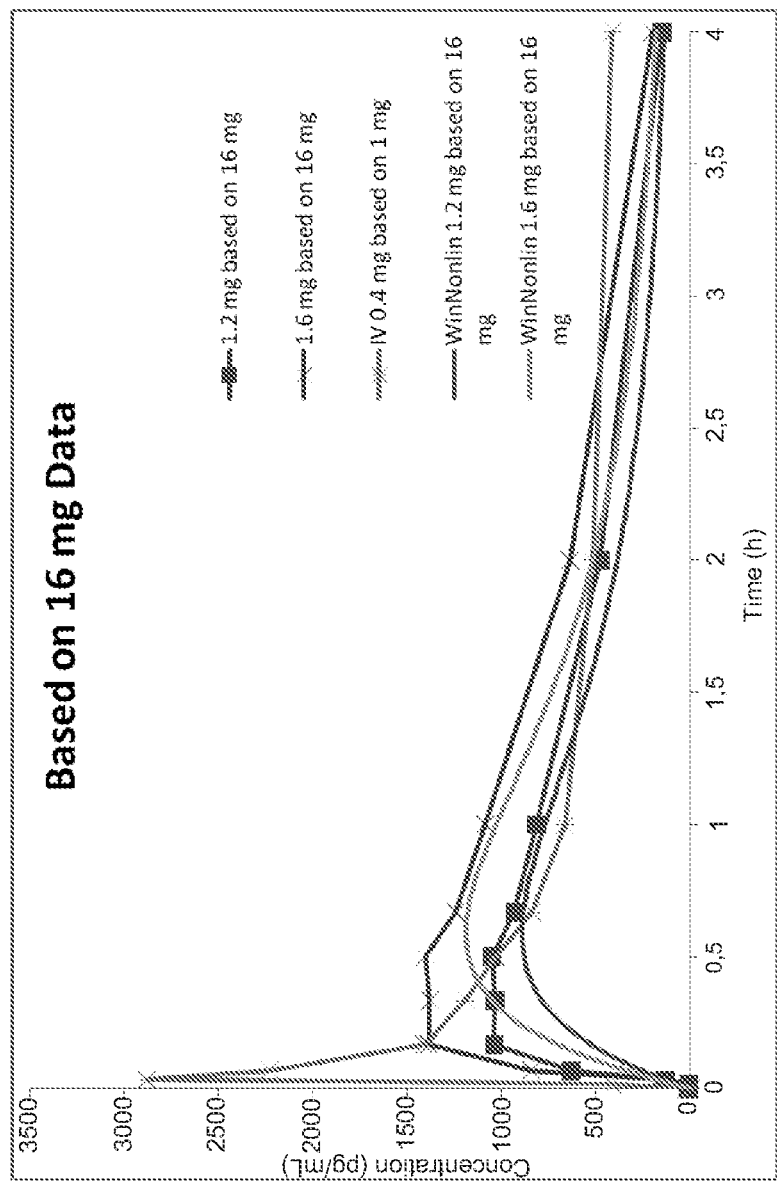
FIG. 16 shows the estimated curves (based on the data of Example 1: 16 mg naloxone HCl applied intranasally) using either Excel or WinNonlin for 1.2 mg naloxone applied intranasally (IN) and 1.6 mg naloxone applied IN for a period of 4 hours as well as for 0.4 mg naloxone applied intravenously (IV, using Excel [wherein, compared to FIG. 8, one outlying subject was excluded]).

Finally, FIGS. 15 and 16 summarize the data of example 3 described above for a period of 4 h.

Particularly FIG. 15 shows that the IN naloxone plasma levels predicted for amounts of 1.2 mg and 1.6 mg, respectively, display a smoother increase with a considerably longer plateau compared to IV administration of 0.4 mg. It is also evident that the IN-curves display a smooth decline following Cmax compared to the IV curve.

The invention claimed is:

1. A method of treating opioid overdosing or at least one symptom thereof, the method comprising intranasally administering a patient in need thereof 100 µl of an intranasal pharmaceutical dosage form comprising naloxone or a pharmaceutically acceptable salt thereof dissolved in an aqueous application fluid in a final concentration equivalent to between 18 mg naloxone HCl per ml aqueous application fluid and 50 mg naloxone HCl per ml aqueous application fluid, wherein the dosage form has a pH of ≤5.5 and does not include a permeability enhancer.

2. The method of claim 1, wherein the final concentration of the naloxone or pharmaceutically acceptable salt thereof is equivalent to between 20 mg naloxone HCl per ml aqueous application fluid and 60 mg naloxone HCl per ml application fluid.

3. The method of claim 1, wherein the final concentration of the naloxone or pharmaceutically acceptable salt thereof is equivalent to between 30 mg naloxone HCl per ml aqueous application fluid and 50 mg naloxone HCl per ml application fluid.

4. The method of claim 1, wherein the final concentration of the naloxone or pharmaceutically acceptable salt thereof is equivalent to 40 mg naloxone HCl per ml aqueous application fluid.

5. The method of claim 1, wherein the aqueous application fluid is water or an aqueous saline solution.

6. The method of claim 1, wherein the dosage form is provided in a single dosing unit or two dosing units, dependent on whether the dosage form is provided by administration to one nostril or by administration to two nostrils.

7. The method of claim 1, wherein the dosage form is a nasal spray, a nasal mucoadhesive dosage form, or a mucosal atomizer device.

8. The method of claim 1, wherein the naloxone or pharmaceutically acceptable salt thereof is the only pharmaceutically active compound in the dosage form.

9. The method of claim 1, wherein the dosage form is co-administered with an intramuscular and/or intravenous dosage form comprising naloxone or a pharmaceutically acceptable salt thereof.

10. The method of claim 7, wherein the dosage form is provided in a single dosing unit for administration administered to one nostril.

11. A method of treating opioid overdosing, the method comprising intranasally administering a patient in need thereof 100 µl of an intranasal pharmaceutical dosage form comprising naloxone or a pharmaceutically acceptable salt thereof dissolved in an aqueous fluid in a final concentration equivalent to 20 mg, 30 mg or 40 mg naloxone HCl per ml aqueous fluid and 50 mg naloxone HCl per ml aqueous fluid, wherein the dosage form has a pH of ≤5.5 and does not include a permeability enhancer.

12. A method of treating opioid overdosing, the method comprising (i) intranasally administering to one nostril of a patient in need thereof 100 µl of an intranasal pharmaceutical dosage form comprising naloxone or a pharmaceutically acceptable salt thereof dissolved in an aqueous fluid in a final concentration equivalent to 20 mg, 30 mg or 40 mg naloxone HCl per ml aqueous fluid and 50 mg naloxone HCl per ml aqueous fluid, wherein the dosage form has a pH of ≤5.5 and does not include a permeability enhancer and (ii) optionally repeating administration until an effective amount of naloxone is reached in the systemic circulation of the patient to counter the effect of the opioid.

13. A method of treating opioid overdosing, the method consisting essentially of (i) intranasally administering to one nostril of a patient in need thereof 100 µl of an intranasal pharmaceutical dosage form comprising naloxone or a pharmaceutically acceptable salt thereof dissolved in an aqueous fluid in a final concentration equivalent to 20 mg, 30 mg or 40 mg naloxone HCl per ml aqueous fluid and 50 mg naloxone HCl per ml aqueous fluid, wherein the dosage form has a pH of ≤5.5 and does not include a permeability enhancer and (ii) optionally repeating administration until an effective amount of naloxone is reached in the systemic circulation of the patient to counter the effect of the opioid.

* * * * *